US005840495A

United States Patent [19]
West et al.

[11] Patent Number: 5,840,495
[45] Date of Patent: *Nov. 24, 1998

[54] METHODS FOR DIAGNOSIS OF CONDITIONS ASSOCIATED WITH ELEVATED LEVELS OF TELOMERASE ACTIVITY

[75] Inventors: Michael D. West, Belmont, Calif.; Jerry Shay, Dallas; Woodring Wright, Arlington, both of Tex.

[73] Assignee: University of Texas System Board of Regents, Austin, Tex.

[*] Notice: The term of this patent shall not extend beyond the expiration date of Pat. No. 5,489,508.

[21] Appl. No.: 480,037

[22] Filed: Jun. 7, 1995

Related U.S. Application Data

[60] Division of Ser. No. 38,766, Mar. 24, 1993, Pat. No. 5,489,508, which is a continuation-in-part of Ser. No. 882,438, May 13, 1992, abandoned.

[51] Int. Cl.⁶ .............................. C12Q 1/68; G01N 33/53
[52] U.S. Cl. .................................... 435/7.1; 435/4; 435/6; 435/15; 435/91.2; 435/91.5; 436/64; 436/501; 935/77; 935/78
[58] Field of Search .............................. 435/6, 91.2, 91.5, 435/7.1, 7.4, 7.2, 7.15; 436/501, 64, 94; 935/77, 78; 536/24.33

[56] References Cited

U.S. PATENT DOCUMENTS

| | | | |
|---|---|---|---|
| 4,737,454 | 12/1988 | Dattagupta et al. | |
| 5,489,508 | 2/1996 | West et al. | 435/6 |
| 5,583,016 | 12/1996 | Villeponteau | 435/91.3 |

FOREIGN PATENT DOCUMENTS 9408053  4/1994  WIPO .

OTHER PUBLICATIONS

Avilion et al, Cancer Research (1996) 56:645–650.

Greider and Blackburn, "A telomeric sequence in the RNA of Tetrahymena telomerase required for telomere repeat synthesis," *Nature* 337:331–337 (1989).

Cotten, "The in vivo application of ribozymes," *Trends in Biotechnology* 8:174–178 (1990).

Harley et al., "The Telomere Hypothesis of Cellular Aging," *Expermiental Gerontology* 27:375–382 (1992).

Shay et al., "Loss of telomeric DNA during aging may predipose cells to cancer (Review)," *Int'l J. Oncology* 3:559–563 (1993).

Windle and McGuire, "Telomeres: the long and the short of it," *Proceedings of the American Association for Cancer Research* 33:594–595 (1992).

Counter et al., "Stabilization of Short Telomeres and Telomerase Activity Accompany Immortalization of Epstein–Barr Virus–Transformed Human B Lymphocytes," *J. Virology* 68:3410–3414 (1994).

Klingelhutz et al., "Restoration of Telomeres in Human Papoillomavirus–Immortalized Human Anogenital Epithelial Cells," *Molecular and Cellular Biology* 14:961–969 (1994).

Counter et al., "Telomerase activity in human ovarian carcinoma," *Proc. Natl. Acad. Sci. USA* 91:2900–2904 (1994).

(List continued on next page.)

Primary Examiner—Carla J. Myers
Attorney, Agent, or Firm—Kevin Kaster; Lyon & Lyon LLP

[57] ABSTRACT

Method and compositions are provided for the determination of telomere length and telomerase activity, as well as the ability to inhibit telomerase activity in the treatment of proliferative diseases. Particularly, primers are elongated under conditions which minimize interference from other genomic sequences, so as to obtain accurate determinations of telomeric length or telomerase activity. In addition, compositions are provided for intracellular inhibition of telomerase activity.

27 Claims, 14 Drawing Sheets

OTHER PUBLICATIONS

Strahl and Blackburn, "The effects of nucleoside analogs on telomerase and telomeres in Tetrahymena," *Nucleic Acids Research* 22:893–900 (1994).

Zahler et al., "Inibition of Telomerase by G–quartet DNA Structures," pp. 718–720, Nature, vol. 350, (Apr. 15, 1991).

Eck and Nabel, "Antisense oligonucleotides for therapeutic intervention", Current Opin. in Biotech, 2:897 (1991).

Harley, "Telomere Loss: Mitotic Clock or Genetic Time Bomb?" 256 Nature 271 (1991).

Yu et al., "Developmentally Programmed Healing of Chromosomes by Telomerase in Tetrahymena," 67 Cell 823 (1991).

Harley et al., "Telomeres Shorten During Ageing of Human Fibroblasts" 345 Nature 458 (1990).

Blackburn, "Structure and Function of Telomeres", 350 Nature 572 (1991).

Cech, "Ribozymes and their medical implications", 260 J. of Amer. Med. Assoc. 3030 (1988).

Harley, Mutation Research, 256:271–282 (1991).

Counter et al., "Telomere shortening associated with chromosome instability is arrested in immortal cells which express telomerase activity," EMBO J 11:1921–1929 (May 5, 1992).

Greider et al.,"Telomerase is Processive", Molecular and Cellular Biology, 11:4572–4580 (1991).

Blackburn et al., "Recognition and Elongation of Telomeres by Telomerase" Genome, 31:553–560 (1989).

Greider and Blackburn, "The telomere terminal transferase of tetrahymena is a ribonucleoprotein enzyme with two kinds of primer specificity," Cell 51:887–898 (1987).

S. Wang and V. Zakian, "Telomere–telomere recombination provides an express pathway for telomere acquisition", Nature 345:456 (1990).

Goldstein, "Replicative senescence: the human fibroblast comes of age", Science 249:1129 (1990).

Smith et al., "Intraclonal variation in proliferative potential of human diploid fibroblasts: stochastic mechanisms for cellular aging", Science 207:82 (1980).

Ohno, "Strict relationship between dialyzed serum concentration and cellular life span" Mechanisms of Aging and Development 11:179 (1979).

Hayflick et al., "The serial cultivation of human diploid cell strains", Experimental Cell Research 25:585 (1961).

Szostak, "The beginning of the ends", Nature 337:303 (1989).

Jankovic et al., "Telomere loss and cancer", Nature 350:197 (1991).

Gall, "Tying up loose ends", Nature 344:108 (1990).

Yu et al., "In vivo alteration of telomere sequences and senescence caused by mutated Tetrahymena telomerase RNAs", Nature 344:126 (1990).

Harrington and Greider, "Telomerase primer specificity and chromosome healing", Nature 353:451 (1991).

Gray et al., "Cloning and expression of genes for the Oxytricha telomere–binding protein specific subunit interactions in the telomeric complex", Cell 67:807.

Muller et al., "New telomere formation after developmentally regulated chromosomal breakage during the process of chromosome diminution in *Ascaris lumbricoides*" Cell 67:815 (1991).

Yu and Blackburn, "Developmentally programmed healing of chromosomes by telomerase in Tetrahymena", cell 67:823 (1991).

Greider, "Telomeres, telomerase and senescence", Bioessays 12:363 (1990).

Hendersen et al., "Telomere G–strand structure and function analyzed by chemical protection, base analogue substitution, and utilization by telomerase in vitro", Biochemistry 29:732 (1990).

Gottschling et al., "Position effect at *S. cerevisiae* telomeres: reversible repression of Pol II transcription", Cell 63:751 (1990).

Lundblad and Szostak, "A mutant with a defect in telomere elongation leads to senescence in yeast", Cell 57:633 (1989).

Blackburn, "The molecular structure of centromeres and telomeres", Annual Reviews in Biochemistry 53:163 (1984).

Olovnikov, "A theory of marginotomy", J. Theoretical Biology 41:181 (1973).

Cooke and Smith, "Variability at the telomeres of the human X/Y pseudoautosomal region", CSHSQB LI:213 (1986).

Greider, "Chromosome first aid", Cell 67:645 (1991).

Morin, "The human telomere terminal transferase enzyme is a ribonucleoprotein that synthesizes TTAGGG repeats", Cell 59:521 (1989).

Ham and McKeehan, "Media and growth requirements", Methods in Enzymology LVIII:44 (1979).

Starling et al., "Extensive telomere repeat arrays in mouse are hypervariable", Nucleic Acids Research 18:6881 (1990).

Allsopp et al., "Telomere length predicts replicative capacity of human fibroblasts," *Proc. Natl. Acad. Sci. USA* 89:10114–10118 (1992).

METHODS FOR DIAGNOSIS OF CONDITIONS ASSOCIATED WITH ELEVATED LEVELS OF TELOMERASE ACTIVITY

This application is a divsion of application Ser. No. 08/038,766 filed Mar. 24, 1993, now U.S. Pat. No. 5,489,508, hereby incorporated by reference herein in totality, including drawing which is a continuation-in-part of Michael D. West et al., entitled "Telomerase Activity Modulation and Telomere Diagnosis", filed May 13, 1992, and assigned U.S. Ser. No. 07/882,438 now abandoned, hereby incorporated by reference herein.

This invention relates to methods for therapy and diagnosis of cellular senescence and immortalization.

BACKGROUND OF THE INVENTION

The following is a general description of art relevant to the present invention. None is admitted to be prior art to the invention. Generally, this art relates to observations relating to cellular aging, and theories or hypotheses which explain such aging and the mechanisms by which cells escape senescence and immortalize.

The finite replicative capacity of normal human cells, e.g., fibroblasts, is characterized by a cessation of proliferation in spite of the presence of serum growth factors. This cessation of replication after a maximum of 50 to 100 population doublings in vitro is referred to as cellular senescence. See, Goldstein, 249 *Science* 1129, 1990; Hayflick and Moorehead, 25 *Exp. Cell Res.* 585, 1961; Hayflick, ibid., 37:614, 1985; Ohno, 11 *Mech. Aging Dev.* 179, 1979; Ham and McKeehan, (1979) "Media and Growth Requirements", W. B. Jacoby and I. M. Pastan (eds), in: *Methods in Enzymology*, Academic Press, N.Y., 58:44–93. The replicative life span of cells is inversely proportional to the in vivo age of the donor (Martin et al., 23 *Lab. Invest.* 86, 1979; Goldstein et al., 64 *Proc. Natl. Acad. Sci. USA* 155, 1969; and Schneider and Mitsui, ibid., 73:3584, 1976), and is therefore suggested to reflect in vivo aging on a cellular level.

Cellular immortalization (unlimited life span) may be thought of as an abnormal escape from cellular senescence. Shay et al., 196 *Exp. Cell Res.* 33, 1991. Normal human somatic cells appear to be mortal, i.e., have finite replication potential. In contrast, the germ line and malignant tumor cells are immortal (have indefinite proliferative potential). Human cells cultured in vitro appear to require the aid of transforming oncoproteins to become immortal and even then the frequency of immortalization is $10^{-6}$ to $10^{-7}$. Shay and Wright, 184 *Exp. Cell Res.* 109, 1989. A variety of hypotheses have been advanced over the years to explain the causes of cellular senescence. While examples of such hypotheses are provided below, there appears to be no consensus or universally accepted hypothesis.

For example, a free radical theory suggests that free radical-mediated damage to DNA and other macromolecules is causative in critical loss of cell function (Harmon, 11 *J. Gerontol.* 298, 1956; Harmon, 16 *J. Gerontol.* 247, 1961). Somatic mutation theories propose that without genetic recombination cells lack the ability to proliferate indefinitely due to a progressive loss of genetic information (Burnet, "Intrinsic Mutagenesis—A Genetic Approach to Aging", Wiley, N.Y., 1976; Hayflick, 27 *Exp. Gerontol.* 363, 1992). The theories concerning genetically programmed senescence suggest that the expression of senescent-specific genes actively inhibit cell proliferation perhaps under the direction of a mitotic clock (Martin et al., 74 *Am. J. Pathol.* 137, 1974; Goldstein, 249 *Science* 1129, 1990).

Smith and Whitney, 207 *Science* 82, 1980, discuss a mechanism for cellular aging and state that their data is:

compatible with the process of genetically controlled terminal differentiation. The gradual decrease in proliferation potential would also be compatible with a continuous build up of damage or errors, a process that has been theorized. However, the wide variability in doubling potentials, especially in mitotic pairs, suggests an unequalled partitioning of damage or errors at division.

Olovnikov, 41 *J. Theoretical Biology* 181, 1973, describes the theory of marginotomy to explain the limitations of cell doubling potential in somatic cells. He states that an:

informative oligonucleotide, built into DNA after a telogene and controlling synthesis of a repressor of differentiation, might serve as a means of counting mitosis performed in the course of morphogenesis. Marginotomic elimination of such an oligonucleotide would present an appropriate signal for the beginning of further differentiation. Lengthening of the telogene would increase the number of possible mitoses in differentiation.

Harley et al., 345 *Nature* 458, 1990, state that the amount and length of telomeric DNA in human fibroblasts decreases as a function of serial passage during aging in vitro, and possibly in vivo, but do not know whether this loss of DNA has a causal role in senescence. They also state:

Tumour cells are also characterized by shortened telomeres and increased frequency of aneuploidy, including telomeric associations. If loss of telomeric DNA ultimately causes cell-cycle arrest in normal cells, the final steps in this process may be blocked in immortalized cells. Whereas normal cells with relatively long telomeres and a senescent phenotype may contain little or no telomerase activity, tumour cells with short telomeres may have significant telomerase activity. Telomerase may therefore be an effective target for anti-tumour drugs.

. . .

There are a number of possible mechanisms for loss of telomeric DNA during ageing, including incomplete replication, degradation of termini (specific or nonspecific), and unequal recombination coupled to selection of cells with shorter telomeres. Two features of our data are relevant to this question. First, the decrease in mean telomere length is about 50 bp per mean population doubling and, second, the distribution does not change substantially with growth state or cell arrest. These data are most easily explained by incomplete copying of the template strands at their 3' termini. But the absence of detailed information about the mode of replication or degree of recombination at telomeres means that none of these mechanisms can be ruled out. Further research is required to determine the mechanism of telomere shortening in human fibroblasts and its significance to cellular senescence. [Citations omitted.]

Hastie et al., 346 *Nature* 866, 1990, while discussing colon tumor cells, state that:

[T]here is a reduction in the length of telomere repeat arrays relative to the normal colonic mucosa from the same patient.

. . .

Firm figures are not available, but it is likely that the tissues of a developed fetus result from 20–50 cell divisions, whereas several hundred or thousands of divisions have produced the colonic mucosa and blood cells of 60-year old individuals. Thus the degree of telomere reduction is more or less proportional to the number of cell divisions. It has been shown that the ends of Drosophila chromosomes without normal telomeres reduce in size by ~4 base pairs (bp) per cell division and that the ends of yeast chromosomes reduce by a similar degree in a mutant presumed to lack telomerase function. If we assume the same rate of reduction is occurring during somatic division in human tissues, then a reduction in THF by 14 kb would mean that 3,500 ancestral cell divisions lead to the production of cells in the blood of a 60-year old individual; using estimates of sperm telomere length found elsewhere we obtain a value of 1,000–2,000. These values compare favourably with those postulated for mouse blood cells. Thus, we propose that telomerase is indeed lacking in somatic tissues. In this regard it is of interest to note that in maize, broken chromosomes are only healed in sporophytic (zygotic) tissues and not in endosperm (terminally differentiated), suggesting that telomerase activity is lacking in the differentiated tissues. [Citations omitted.]

The authors propose that in some tumors telomerase is reactivated, as proposed for HeLa cells in culture, which are known to contain telomerase activity. But, they state:

One alternative explanation for our observations is that in tumours the cells with shorter telomeres have a growth advantage over those with larger telomeres, a situation described for vegetative cells of tetrahymena. [Citations omitted.]

Harley, 256 *Mutation Research* 271, 1991, discusses observations allegedly showing that telomeres of human somatic cells act as a mitotic clock shortening with age both in vitro and in vivo in a replication dependent manner. He states:

Telomerase activation may be a late, obligate event in immortalization since many transformed cells and tumour tissues have critically short telomeres. Thus, telomere length and telomerase activity appear to be markers of the replicative history and proliferative potential of cells; the intriguing possibility remains that telomere loss is a genetic time bomb and hence causally involved in cell senescence and immortalization.

. . .

Despite apparently stable telomere length in various tumour tissues or transformed cell lines, this length was usually found to be shorter than those of the tissue of origin. These data suggest that telomerase becomes activated as a late event in cell transformation, and that cells could be viable (albeit genetically unstable) with short telomeres stably maintained by telomerase. If telomerase was constitutively present in a small fraction of normal cells, and these were the ones which survived crisis or became transformed, we would expect to find a greater frequency of transformed cells with long telomeres. [Citations omitted.]

He proposes a hypothesis for human cell aging and transformation as "[a] semi-quantitative model in which telomeres and telomerase play a causal role in cell senescence and cancer" and proposes a model for this hypothesis.

De Lange et al., 10 *Molecular and Cellular Biolocy* 518, 1990, generally discuss the structure of human chromosome ends or telomeres. They state:

we do not know whether telomere reduction is strictly coupled to cellular proliferation. If the diminution results from incomplete replication of the telomere, such a coupling would be expected; however, other mechanisms, such as exonucleolytic degradation, may operate independent of cell division. In any event, it is clear that the maintenance of telomeres is impaired in somatic cells. An obvious candidate activity that may be reduced or lacking is telomerase. A human telomerase activity that can add TTAGGG repeats to G-rich primers has recently been identified (G. Morin, personal communication). Interestingly, the activity was demonstrated in extracts of HeLa cells, which we found to have exceptionally long telomeres. Other cell types have not been tested yet, but such experiments could now establish whether telomerase activity is (in part) responsible for the dynamics of human chromosome ends.

Starling et al., 18 *Nucleic Acids Research* 6881, 1990, indicate that mice have large telomeres and discusses this length in relationship to human telomeres. They state:

Recently it has been shown that there is reduction in THF length with passage number of human fibroblasts in vitro and that cells in a senescent population may lack telomeres at some ends altogether. Thus in vitro, telomere loss may play a role in senescence, a scenario for which there is evidence in *S. cerevisae* and Tetrahymena. Some of the mice we have been studying are old in mouse terms, one and a half years, yet they still have THF's greater than 30 kb in all tissues studied. In humans, telomeres shorten with age at a rate of 100 bp per year, hence, it is conceivable that the same is happening in the mouse, but the removal of a few 100 bps of terminal DNA during its lifetime would not be detectable. [Citations omitted.] D'Mello and Jazwinski, 173 *J. Bacteriolocy* 6709, 1991, state:

We propose that during the life span of an organism, telomere shortening does not play a role in the normal aging process. However, mutations or epigenetic changes that affect the activity of the telomerase, like any other genetic change, might affect the life span of the individual in which they occur.

. . .

In summary, the telomere shortening with age observed in human diploid fibroblasts may not be a universal phenomenon. Further studies are required to examine telomere length and telomerase activity not only in different cell types as they age but also in the same cell type in different organisms with differing life spans.

This would indicate whether telomere shortening plays a causal role in the senescence of a particular cell type or organism.

Hiyama et al., 83 *Jpn. J. Cancer Res.* 159, 1992, provide findings that "suggest that the reduction of telomeric repeats is related to the proliferative activity of neuroblastoma cells and seems to be a useful indicator of the aggressiveness of neuroblastoma. Although we do not know the mechanism of the reduction and the elongation of telomeric repeats in neuroblastoma, we can at least say that the length of telomeric repeats may be related to the progression and/or regression of neuroblastoma."

Counter et al., 11 *EMBO J.* 1921, 1992, state "loss of telomeric DNA during cell proliferation may play a role in ageing and cancer." They propose that the expression of telomerase is one of the events required for a cell to acquire immortality and note that:

This model may have direct relevance to tumourigenesis in vivo. For example, the finite lifespan of partially transformed (pre-immortal) cells which lack telomerase might explain the frequent regression of tumours after limited growth in vivo. In bypassing the checkpoint representing normal replicative senescence, transformation may confer an additional 20–40 population doublings during which an additional ≈2 kbp of telomeric DNA is lost. Since 20–40 doublings ($10^6$-$10^{12}$ cells in a clonal population) potentially represents a wide range of tumour sizes, it is possible that many benign tumours may lack telomerase and naturally regress when telomeres become critically shortened. We predict that more aggressive, perhaps metastatic tumours would contain immortal cells which express telomerase. To test this hypothesis, we are currently attempting to detect telomerase in a variety of tumour tissues and to correlate activity with proliferative potential. Anti-telomerase drugs or mechanisms to repress telomerase expression could be effective agents against tumours which depend upon the enzyme for maintenance of telomeres and continued cell growth.

Levy et al., 225 *J. Mol. Biol.* 951, 1992, state that:

Although it has not been proven that telomere loss contributes to senescence of multicellular organisms, several lines of evidence suggest a causal relationship may exist.

. . .

It is also possible that telomere loss with age is significant in humans, but not in mice. [Citations omitted.]

Windle and McGuire, 33 *Proceedings of the American Association for Cancer Research* 594, 1992, discuss the role of telomeres and state that:

These and other telomere studies point in a new direction regarding therapeutic targets and strategies to combat cancer. If the cell can heal broken chromosomes preventing genomic disaster, then there may be a way to facilitate or artificially create this process. This could even provide a preventive means of stopping cancer which could be particularly applicable in high risk patients. The difference in telomere length in normal versus tumor cells also suggests a strategy where the loss of telomeres is accelerated. Those cells with the shortest telomeres, such as those of tumor metastasis would be the most susceptible.

Goldstein, 249 *Science* 1129, 1990, discusses various theories of cellular senescence including that of attrition of telomeres. He states:

However, such a mechanism is not easily reconciled with the dominance of senescent HDF over young HDF in fusion hybrids, particularly in short-term heterokaryons. One could again invoke the concept of dependence and the RAD9 gene example, such that complete loss of one or a few telomeres leads to the elaboration of a negative signal that prevents initiation of DNA synthesis, thereby mimicking the differentiated state. This idea, although speculative, would not only explain senescent replicative arrest but also the chromosomal aberrations observed in senescent HDS that would specifically ensue after loss of telomeres. [Citations omitted.]

The role of telomere loss in cancer is further discussed by Jankovic et al. and Hastie et al., both at 350 *Nature* 1991, in which Jankovic indicates that telomere shortening is unlikely to significantly influence carcinogenesis in men and mice. Hastie et al. agree that if telomere reduction does indeed reflect cell turnover, this phenomenon is unlikely to play a role in pediatric tumors, and those of the central nervous system. Hastie et al., however, feel "our most original and interesting conclusion was that telomere loss may reflect the number of cell divisions in a tissue history, constituting a type of clock.

Kipling and Cooke, 1 *Human Molecular Genetics* 3, 1992, state:

It has been known for some years that telomeres in human germline cells (e.g. sperm) are longer than those in somatic tissue such as blood. One proposed explanation for this is the absence of telomere repeat addition (i.e. absence of telomerase activity) in somatic cells. If so, incomplete end replication would be expected to result in the progressive loss of terminal repeats as somatic cells undergo successive rounds of division. This is indeed what appears to happen in vivo for humans, with both blood and skin cells showing shorter telomeres with increasing donor age, and telomere loss may contribute to the chromosome aberrations typically seen in senescent cells. Senescence and the measurement of cellular time is an intriguingly complex subject and it will be interesting to see to what extent telomere shortening has a causal role. The large telomeres possessed by both young and old mice would seem to preclude a simple relationship between telomere loss and aging, but more elaborate schemes cannot be ruled out. [Citations omitted.]

Greider, 12 *BioEssays* 363, 1990, provides a review of the relationship between telomeres, telomerase, and senescence. She indicates that telomerase contains an RNA component which provides a template for telomere repeat synthesis. She notes that an oligonucleotide "which is complementary to the RNA up to and including the CAACCCCAA sequence, competes with d(TTGGGG)n primers and inhibits telomerase in vitro" (citing Greider and Blackburn, 337 *Nature* 331, 1989). She also describes experiments which she believes provide direct evidence that telomerase is involved in telomere synthesis in vivo." She goes on to state:

Telomeric restriction fragments in many transformed cell lines are much shorter than those in somatic cells. In addition, telomere length in tumor tissues is significantly shorter than in the adjacent non-tumor tissue. When transformed cell lines are passaged in vitro there is no change in telomere length. Thus if untransformed cells lack the ability to maintain a telomere length equilibrium, most transformed cells appear to regain it and to reset the equilibrium telomere length to a size shorter than seen in most tissues in vivo. The simplest interpretation of these data is that enzymes, such as telomerase, involved in maintaining telomere length may be required for growth of transformed cells and not required for normal somatic cell viability. This suggests that telomerase may be a good target for anti-tumor drugs. [Citations omitted.]

Blackburn, 350 *Nature* 569, 1991, discusses the potential for drug action at telomeres stating:

The G-rich strand of the telomere is the only essential chromosomal DNA sequence known to be synthesized by the copying of a separate RNA sequence. This unique mode of synthesis, and the special structure and behavior of telomeric DNA, suggest that telomere synthesis could be a target for selective drug action. Because telomerase activity seems to be essential for protozoans or yeast, but not apparently for mammalian somatic cells, I propose that telomerase should be explored as a target for drugs against eukaryotic pathogenic or parasitic microorganisms, such as parasitic protozoans or pathogenic yeasts. A drug that binds telomerase selectively, either through its reverse-transcriptase or DNA substrate-binding properties, should selectively act against prolonged maintenance of the dividing lower eukaryote, but not impair the mammalian host over the short term, because telomerase activity in its somatic cells may normally be low or absent. Obvious classes of drugs to investigate are those directed specifically against reverse transcriptases as opposed to other DNA or RNA polymerases, and drugs that would bind telomeric DNA itself. These could include drugs that selectively bind the G—G base-paired forms of the G-rich strand protrusions at the chromosome termini, or agents which stabilize an inappropriate G—G base-paired form, preventing it from adopting a structure necessary for proper function in vivo. Telomeres have been described as the Achilles heel of chromosomes: perhaps it is there that drug strategies should now be aimed. [Citations omitted.]

Shay et al., 27 *Experimental Gerontology* 477, 1992, and 196 *Exp. Cell Res.* 33, 1991 describe a two-stage model for human cell mortality to explain the ability of Simian Virus 40 Tag to immortalize human cells. The mortality stage 1 mechanism (M1) is the target of certain tumor virus proteins, and an independent mortality stage 2 mechanism (M2) produces crisis and prevents these tumor viruses from directly immortalizing human cells. The authors utilized T-antigen driven by a mouse mammary tumor virus promoter to cause reversible immortalization of cells. The Simian Virus 40 T-antigen is said to extend the replicative life span of human fibroblast by an additional 40–60%. The authors postulate that the M1 mechanism is overcome by T-antigen binding to various cellular proteins, or inducing new activities to repress the M1 mortality mechanism. The M2 mechanism then causes cessation of proliferation, even though the M1 mechanism is blocked. Immortality is achieved only when the M2 mortality mechanism is also disrupted.

Other review articles concerning telomeres include Blackburn and Szostak, 53 *Ann. Rev. Biochem.* 163, 1984; Blackburn, 350 *Nature* 569, 1991; Greider, 67 *Cell* 645, 1991; and Mayzis 265 *Scientific American* 48, 1991. Relevant articles on various aspects of telomeres include Cooke and Smith, *Cold Siring Harbor Symposia on Quantitative Biology* Vol. LI, pp. 213–219; Morin, 59 *Cell* 521, 1989; Blackburn et al., 31 *Genome* 553, 1989; Szostak, 337 *Nature* 303, 1989; Gall, 344 *Nature* 108, 1990; Henderson et al., 29 *Biochemistry* 732, 199–0; Gottschling et al., 63 *Cell* 751, 1990; Harrington and Grieder, 353 *Nature* 451, 1991; Muller et al., 67 *Cell* 815, 1991; Yu and Blackburn, 67 *Cell* 823, 1991; and Gray et al., 67 *Cell* 807, 1991. Other articles or discussions of some relevance include Lundblad and Szostak, 57 *Cell* 633, 1989; and Yu et al., 344 *Nature* 126, 1990.

SUMMARY OF THE INVENTION

This invention concerns therapies associated with control of telomere length and telomerase activity. Therapeutic strategies of this invention include reducing the rate or absolute amount of telomere length loss during cell proliferation, thereby providing for the postponement of cellular senescence and reducing the level of chromosomal fusions and other chromosomal aberrations. In addition, inhibition of telomerase activity in vivo or in vitro may be used to control diseases associated with cell immortalization, such as neoplasia.

The invention also concerns the determination of cellular status by analysis of telomere length and telomerase activity, as a diagnostic of cellular capacity for proliferation. Assays for telomere length are performed to provide useful information on the relative age and remaining proliferative capability of a wide variety of cell types in numerous tissues. Telomerase activity and the presence of the enzyme is used as a marker for diagnosing and staging neoplasia.

Applicant has determined that inhibition of telomerase activity in a cell in vitro is causally related to reducing the ability of that cell to proliferate. Applicant has also determined that inhibition of telomere shortening in a cell in vitro is causally related to increasing the ability of that cell to proliferate. Thus, applicant is the first to provide data which clearly indicates that inhibition of telomere shortening in vivo or in vitro, and that inhibition of telomerase activity in vivo or in vitro, is therapeutically beneficial. Prior to applicant's experiments, as indicated above, there was no consensus by those in the art that one could predict that such experiments would provide the data observed by applicant, or that such manipulations would have therapeutic utility.

In addition, applicant's experiments have, for the first time, determined a causal relationship between telomerase activity and the ability of a cell to proliferate in an immortal fashion, as well as a causal relationship between telomere length and the potential remaining life span of a cell. As noted above, there was no consensus in the art that one could predict that such a relationship existed. In contrast, applicant has defined this relationship, and thus has now defined useful therapeutic tools by which to determine diagnostically useful data. Such data can be used to define a therapeutic protocol, or the futility of such a protocol.

Thus, in the first aspect, the invention features a method for treatment of a condition associated with an elevated level of telomerase activity within a cell. The method involves administering to that cell a therapeutically effective amount of an inhibitor of telomerase activity.

The level of telomerase activity can be measured as described below, or by any other existing method or equivalent method. By "elevated level" of such activity is meant that the absolute level of telomerase activity in the particular cell is elevated compared to normal cells in that individual, or compared to normal cells in other individuals not suffering from the condition. Examples of such conditions include cancerous conditions, or conditions associated with the presence of cells which are not normally present in that individual, such as protozoan parasites or opportunistic pathogens, and which have some level of telomerase activity. Administration of an inhibitor can be achieved by any desired means well known to those of ordinary skill in the art.

In addition, the term "therapeutically effective amount" of an inhibitor is a well recognized phrase. The amount actually applied will be dependent upon the individual or animal to which treatment is to be applied, and will preferably be an optimized amount such that an inhibitory effect is achieved without significant side-effects (to the extent that those can be avoided by use of the inhibitor). That is, if effective inhibition can be achieved with no side-effects with the inhibitor at a certain concentration, that concentration should be used as opposed to a higher concentration at which side-effects may become evident. If side-effects are unavoidable, however, the minimum amount of inhibitor that is necessary to achieve the inhibition desired should be used.

By "inhibitor" is simply meant any reagent, drug or chemical which is able to inhibit telomerase activity in vitro or in vivo . Such inhibitors can be readily identified using standard screening protocols in which a protein or other moiety having telomerase activity is placed in contact with a potential inhibitor, and the level of telomerase activity measured in the presence or absence of the inhibitor, or in the presence of varying amounts of inhibitor. In this way, not only can useful inhibitors be identified, but the optimum level of such an inhibitor can be determined in vitro.

One example of a suitable telomerase inhibitor assay is carried out in 96-well microtiter plates. One microtiter plate is used to make dilutions of the test compounds, while another plate is used for the actual assay. Duplicate reactions of each sample are performed. A mixture is made containing the appropriate amount of buffer, template oligonucleotide, and telomerase extract for the number of the samples to be tested, and aliquots are placed in the assay plate. The test compounds are added individually and the plates are pre-incubated at 30° C. The $^{32}$P-dGTP is then added and the reaction allowed to proceed for 10 minutes at 30° C. The total volume of each reaction is 10 µl. The reaction is then terminated by addition of Tris and EDTA, and half the volume (5 µl) spotted onto DE81 filter paper. The samples are allowed to air dry and then the filter paper is rinsed in 0.5M sodium phosphate several times to wash away the unincorporated labeled nucleotide. After drying, the filter paper is exposed to a phosphor imaging plate and the amount of signal quantitated. By comparing the amount of signal for each of the test samples to control samples, the percent of inhibition can be determined. This assay has been used to find compounds active as inhibitors, e.g., oxolinic acid, nalidixic acid and AZT.

In addition, a large number of potential telomerase inhibitors can be screened in a single test, since it is inhibition of telomerase activity that is desired. Thus, if a panel of 1,000 potential inhibitors is to be screened, all 1,000 potential inhibitors can be placed into microtiter wells. If a telomerase an inhibitor is discovered, then the pool of 1,000 can be subdivided into 10 pools of 100 and the process repeated until an individual inhibitor is identified. As discussed herein, one particularly useful inhibitor includes oligonucleotides which are able to either bind with the RNA present in telomerase or able to prevent binding of that RNA to its DNA target. Even more preferred are those oligonucleotides which cause inactivation or cleavage of the RNA present in a telomerase. That is, the oligonucleotide is chemically modified or has enzyme activity which causes such cleavage. The above screening may include screening of a pool of many different such oligonucleotide sequences.

In a second aspect, the invention features a method for treatment of a condition associated with an increased rate of proliferation of a cell, e.g., telomere repeat loss associated with cell proliferation in the absence of telomerase. The method involves administering to the cell a therapeutically effective amount of an agent active to reduce loss of telomere length within the cell during its proliferation. Such therapeutics may be especially applicable to conditions of increased cell proliferation.

By "increased rate of proliferation" of a cell is meant that that cell has a higher rate of cell division compared to normal cells of that cell type, or compared to normal cells within other individuals of that cell type. Examples of such cells include the CD4$^+$ cells of HIV-infected individuals (see example below), connective tissue fibroblasts associated with degenerative joint diseases, age-related macular degeneration, astrocytes associated with Alzheimer's Disease and endothelial cells associated with atherosclerosis (see example below). In each case, one particular type of cell or a group of cells is found to be replicating at an increased level compared to surrounding cells in those tissues, or compared to normal individuals, e.g., individuals not infected with the HIV virus. Thus, the invention features administering to those cells an agent which reduces loss of telomere length in those cells while they proliferate. The agent itself need not slow the proliferation process, but rather allow that proliferation process to continue for more cell divisions than would be observed in the absence of the agent. The agent may also be useful to slow telomere repeat loss occurring during normal aging, and for reducing telomere repeat loss while expanding cell number ex vivo for cell-based therapies.

Again, as described above, useful agents can be readily identified by those of ordinary skill in the art using routine screening procedures. For example, a particular cell having a known telomere length is chosen and allowed to proliferate, and the length of telomere is measured during proliferation. Agents which are shown to reduce the loss of telomere length during such proliferation are useful in this invention. Particular examples of such agents are provided below. For example, oligonucleotides which are able to promote synthesis of DNA at the telomere ends are useful in this invention. In addition, telomerase may be added to a cell either by gene therapy techniques, or by injection of the enzyme or its equivalent into a cell.

In related aspects, the invention features pharmaceutical compositions which include therapeutically effective amounts of the inhibitors or agents described above, in pharmaceutically acceptable buffers much as described below. These pharmaceutical compositions may. include one or more of these inhibitors or agents, and be co-administered with other drugs. For example, AZT is commonly used for treatment of HIV, and may be co-administered with an inhibitor or agent of the present invention.

In a related aspect, the invention features a method for extending the ability of a cell to replicate. In this method, a replication extending amount of an agent which is active to reduce loss of telomere length within the cell is provided during cell. replication. As will be evident to those of ordinary skill in the art, this agent is similar to that useful for treatment of a condition associated with an increased rate of proliferation of a cell. However, this method is useful for the treatment of individuals not suffering from any particular condition, but in which one or more cell types are limiting in that patient, and whose life can be extended by extending the ability of those cells to continue replication. That is, the agent is added to delay the onset of cell senescence characterized by the inability of that cell to replicate further in an individual. One example of such a group of cells includes lymphocytes present in patients suffering from Down's Syndrome (although treatment of such cells may also be useful in individuals not identified as suffering from any particular condition or disease, but simply recognizing that one or more cells, or collections of cells are becoming limiting in the life span of that individual).

It is notable that administration of such inhibitors or agents is not expected to be detrimental to any particular individual. However, should gene therapy be used to introduce a telomerase into any particular cell population, care should be taken to ensure that the activity of that telomerase is carefully regulated, for example, by use of a promoter which can be regulated by. the nutrition of the patient. Thus, for example, the promoter may only be activated when the patient eats a particular nutrient, and is otherwise inactive. In this way, should the cell population become malignant, that individual may readily inactivate replication of the cell and cause it to become senescent simply by no longer eating that nutrient.

In a further aspect, the invention features a method for diagnosis of a condition in a patient associated with an elevated level of telomerase activity within a cell. The method involves determining the presence or amount of telomerase within the cells in that patient.

In yet another aspect, the invention features a method for diagnosis of a condition associated with an increased rate of proliferation in that cell in an individual. Specifically, the method involves determining the length of telomeres within the cell.

The various conditions for which diagnosis is possible are described above. As will be exemplified below, many methods exist for measuring the presence or amount of telomerase within a cell in a patient, and for determining the length of telomeres within the cell. It will be evident that the presence or amount of telomerase may be determined within an individual cell, and for any particular telomerase activity (whether it be caused by one particular enzyme or a plurality of enzymes). Those in the art can readily formulate antibodies or their equivalent to distinguish between each type of telomerase present within a cell, or within an individual. In addition, the length of telomeres can be determined as an average length, or as a range of lengths much as described below. Each of these measurements will give precise information regarding the status of any particular individual.

Thus, applicant's invention has two prongs—a diagnostic and a therapeutic prong. These will now be discussed in detail.

The therapeutic prong of the invention is related to the now clear observation that the ability of a cell to remain immortal lies in the ability of that cell to maintain or increase the telomere length of chromosomes within that cell. Such a telomere length can be maintained by the presence of sufficient activity of telomerase, or an equivalent enzyme, within the cell. Thus, therapeutic approaches to reducing the potential of a cell to remain immortal focus on the inhibition of telomerase activity within those cells in which it is desirable to cause cell death. Examples of such cells include cancerous cells, which are one example of somatic cells which have regained the ability to express telomerase, and have become immortal. Applicant has now shown that such cells can be made mortal once more by inhibition of telomerase activity. As such, inhibition can be achieved in a multitude of ways including, as illustrated below, the use of oligonucleotides which, in some manner, block the ability of telomerase to extend telomeres in vivo.

Thus, oligonucleotides can be designed either to bind to a telomere (to block the ability of telomerase to bind to that telomere, and thereby extend that telomere), or to bind to the resident oligonucleotide (RNA) present in telomerase to thereby block telomerase activity on any nucleic acid (telomere). Such oligonucleotides may be formed from naturally occurring nucleotides, or may include modified nucleotides to either increase the stability of the therapeutic agent, or cause permanent inactivation of the telomerase. In addition, non-oligonucleotide based therapies can be readily devised by screening for those molecules which have an ability to inhibit telomerase activity in vitro, and then using those molecules in vivo. Such a screen is readily performed and will provide a large number of useful therapeutic molecules. These molecules may be used for treatment of cancers, of any type, including solid tumors and leukemias (including those in which cells are immortalized, including: apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, merkel cell, mucinous, non-small cell lung, oat cell, papillary, scirrhous, bronchiolar, bronchogenic, squamous cell, and transitional cell), histiocytic disorders, leukemia (e.g., b-cell, mixed-cell, null-cell, T-cell, T-cell chronic, HTLV-II-associated, lyphocytic acute, lymphocytic chronic, mast-cell, and myeloid), histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, chondrosarcoma, cystosarcoma phyllodes, hemangiosarcoma, leukosarcoma, myxosarcoma, rhabdomyosarcoma, sarcoma (e.g., experimental, Kaposi's, and mast-cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervix dysplasia), and for treatment of other conditions in which cells have become immortalized.

Applicant has also determined that it is important to slow the loss of telomere sequences, in particular, cells in association with certain diseases (although such treatment is not limited to this, and can be used in normal aging and ex vivo treatments). For example, some diseases are manifest by the abnormally fast rate of proliferation of one or more particular groups of cells. Applicant has determined that it is the senescence of those groups of cells at an abnormally early age (compared to the age of the patient), that eventually leads to death of that patient. One example of such a disease is AIDS, in which death is caused by the early senescence of $CD4^+$ cells. It is important to note that such cells age, not because of abnormal loss of telomere sequences (although this may be a factor), but rather because the replicative rate of the $CD4^+$ cells is increased such that telomere attrition is caused at a greater rate than normal for that group of cells. Thus, applicant provides therapeutic agents which can be used for treatment of such diseases, and also provides a related diagnostic procedure by which similar diseases can be detected so that appropriate therapeutic protocols can be devised and followed.

Specifically, the loss of telomeres within any particular cell population can be reduced by provision of an oligonucleotide which reduces the extent of telomere attrition during cell division, and thus increases the number of cell divisions that may occur before a cell becomes senescent.

Other reagents, for example, telomerase, may be provided within a cell in order to reduce telomere loss, or to make that cell immortal. Those of ordinary skill in the art will recognize that other enzymatic activities may be used to enhance the lengthening of telomeres within such cells, for example, by providing. certain viral sequences within a cell. In addition, equivalent such molecules, or other molecules may be readily screened to determine those that will reduce loss of telomeres. Such screens may occur in vitro, and the therapeutic agents discovered by such screening utilized in the above method in vivo. with regard to diagnostic procedures, examples of such procedures become evident from the discussion above with regard to therapy. Applicant has determined that the length of the telomere is indicative of the life expectancy of a cell containing that telomere, and of an individual containing that cell. Thus, the length of a telomere is directly correlated to the life span of an individual cell. As discussed above, certain populations of cells may lose telomeres at a greater rate than the other cells within an individual, and those cells may thus become age-limiting within an individual organism. However, diagnostic procedures can now be developed (as described herein) which can be used to indicate the potential life span of any individual cell type, and to follow telomere loss so that a revised estimate to that life span can be made with time.

In certain diseases, for example, the AIDS disease discussed above, it would, of course, be important to follow the telomere length in $CD4^+$ cells. In addition, the recognition that $CD4^+$ cells are limiting in such individuals allows a therapeutic protocol to be devised in which $CD4^+$ cells can be removed from the individual at an early age when AIDS is first detected, stored in a bank, and then reintroduced into the individual at a later age when that individual no longer has the required $CD4^+$ cells available. Thus, an individual's life can be extended by a protocol involving continued administration of that individual's limiting cells at appropriate time points. These appropriate points can be determined by following $CD4^+$ cell senescence, or by determining the length of telomeres within such $CD4^+$ cells (as an indication of when those cells will become senescent). In this way, rather than wait until a cell becomes senescent (and thereby putting an individual at risk of death) telomere length may be followed until the length is reduced below that determined to be pre-senescent, and thereby the timing of administration of new $CD4^+$ cells can be optimized.

Thus, the diagnostic procedures of this invention include procedures in which telomere length in different cell populations is measured to determine whether any particular cell population is limiting in the life span of an individual, and then determining a therapeutic protocol to insure that such cells are no longer limiting to that individual. In addition, such cell populations may be specifically targeted by specific drug administration to insure that telomere length loss is reduced, as discussed above.

Other diagnostic procedures include measurement of telomerase activity as an indication of the presence of immortal cells within an individual. A more precise measurement of such immortality is the presence of the telomerase enzyme itself. Such an enzyme can be readily detected using standard procedures, including assay of telomerase activities, but also by use of antibodies to telomerase, or by use of oligonucleotides that bind the nucleic acid (RNA) present in telomerase. The presence of telomerase is indicative of cells which are metastatic, and such a diagnostic allows pinpointing of such metastatic cells, much as CD44 is alleged to do so. See, Leff, 3(217) BioWorld Today 1, 3, 1992.

It is evident that the diagnostic procedures of the present invention provide the first real method for determining how far certain individuals have progressed in a certain disease. For example, in the AIDS disease, this is the first methodology which allows prior determination of the time at which an HIV positive individual will become immunocompromised. This information is useful for determining the timing of drug administration, such as AZT administration, and will aid in development of new drug regimens or therapies. In addition, the determination of the optimum timing of administration of certain drugs will reduce the cost of treating an individual, reduce the opportunity for the drug becoming toxic to the individual, and reduce the potential for the individual developing resistance to such a drug.

Other features and advantages of the invention will be apparent from the following description of the preferred embodiments thereof, and from the claims.

DESCRIPTION OF THE PREFERRED EMBODIMENTS

The drawings will first briefly be described.

Drawings

Figure 7:
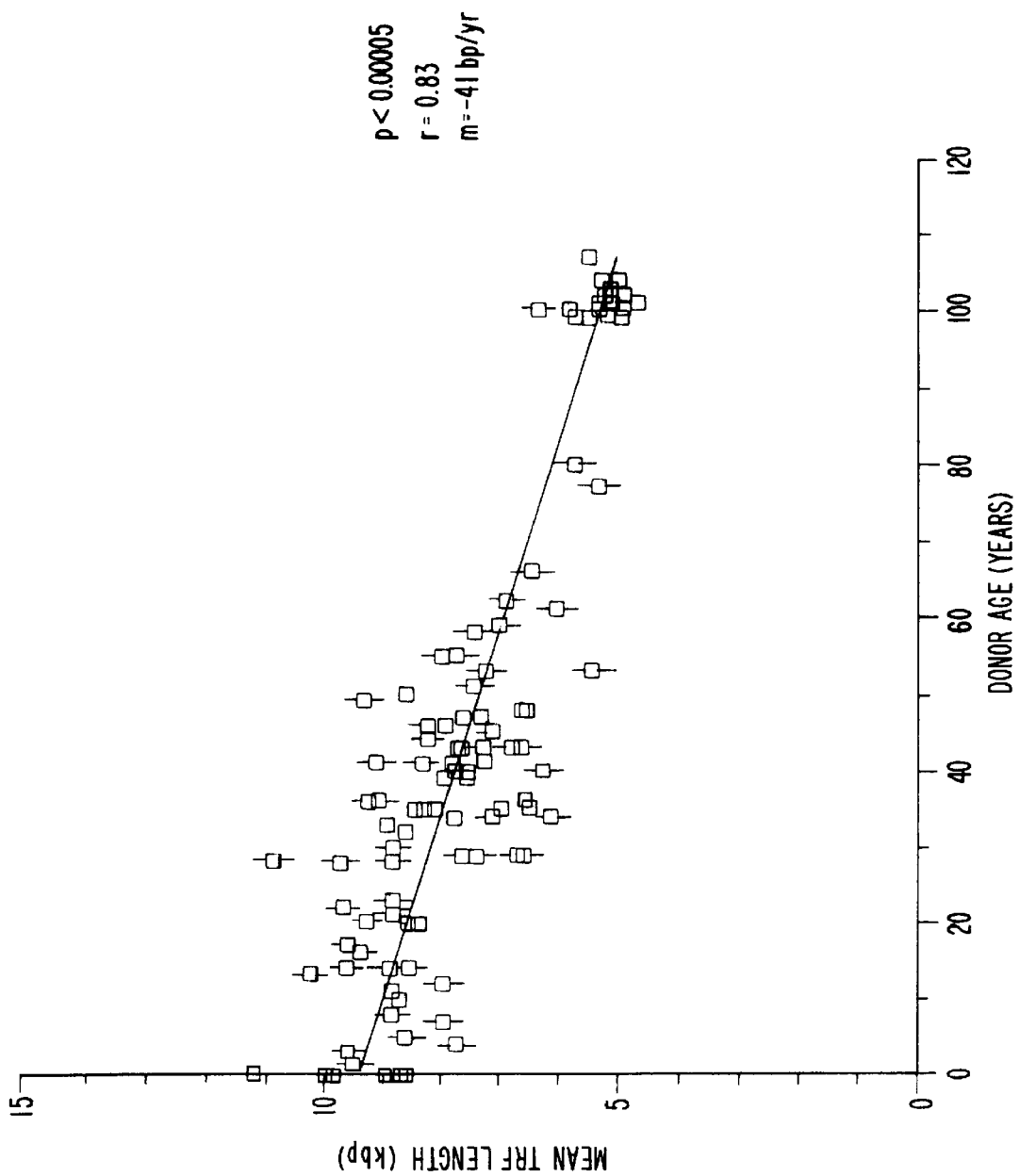
FIG. 7 is a plot of mean TRF length from quantitative analysis of autoradiograms of PBLs plotted as a function of donor age. The slope of the linear regression line ($-41\pm2.6$ bp/y) is significantly different from 0 ($p<0.00005$).
Figure 8:
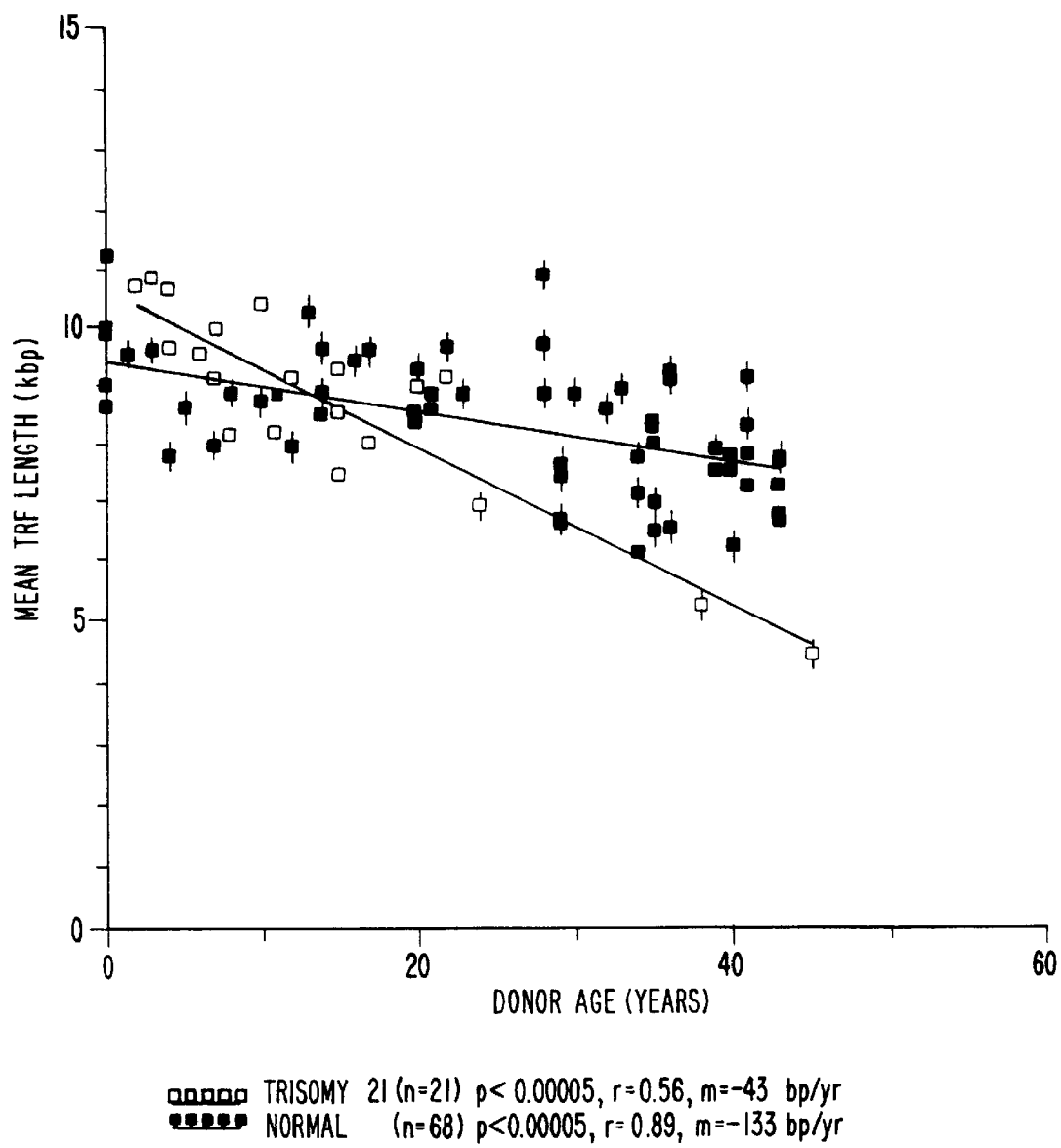

FIG. 8 is a plot showing accelerated telomere loss in Down's Syndrome (DS) patients. Genomic DNA isolated from PBS of DS patients was analyzed as described in FIG. 7. Mean TRF length is shown as a function of donor age, for DS patients (open squares), and age matched controls (■). The slope of the linear regression lines ($-133\pm15$ bp/y, trisomy, vs $-43\pm7.7$, normals) are significantly different ($p<0.0005$).

Figure 9:
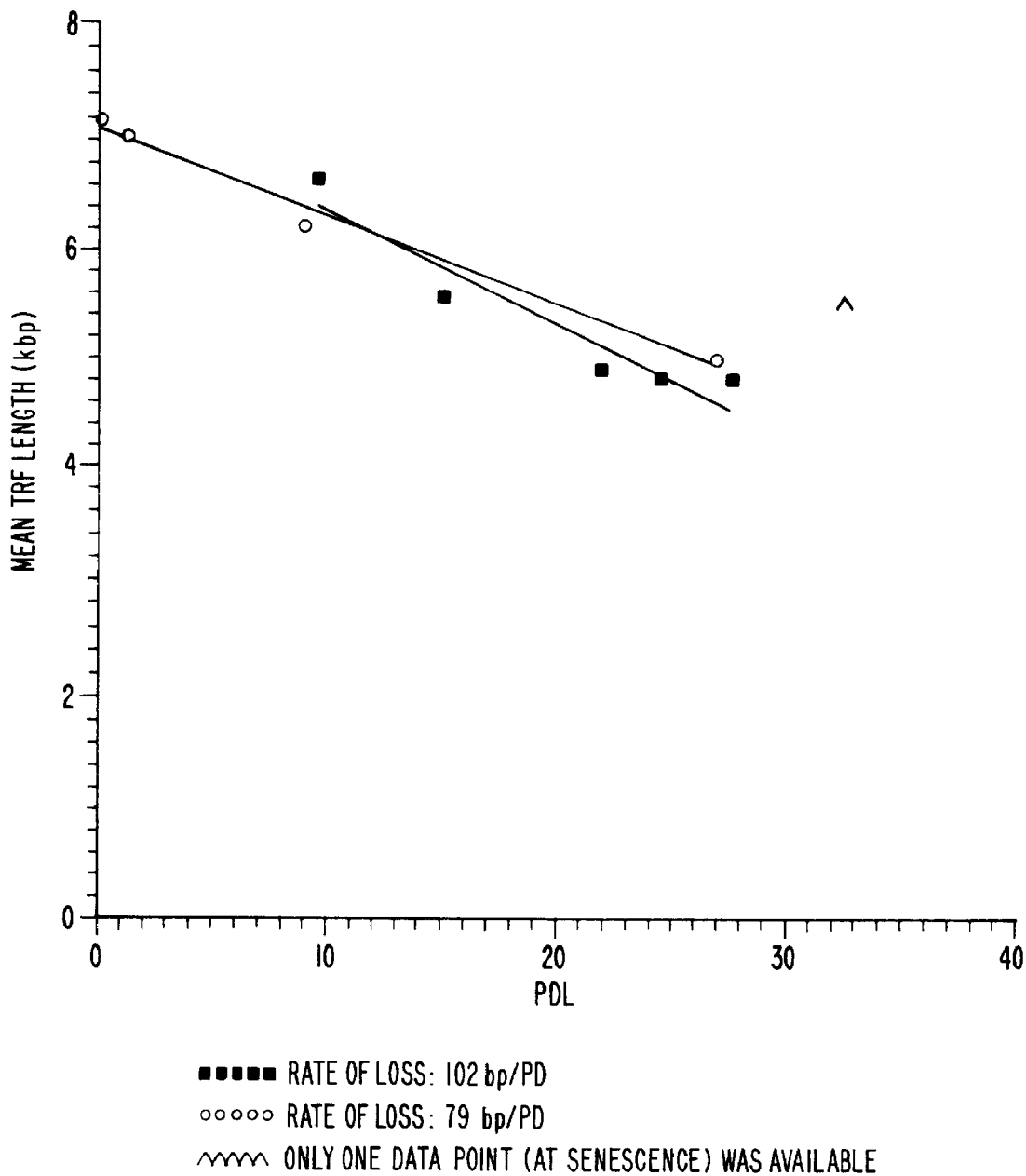

FIG. 9 is a plot showing decrease in mean TRF length as a function of population doublings (shown for DNA from two normal individuals). Donor ages for these cells were not available. The slopes of these lines ($-80\pm19$ (■) and $-102\pm5.4$ (O) bp/doubling) are significantly different from zero ($p<0.0001$). Mean TRF length at terminal passage from a third donor for which multiple passages were not available is also shown (upsidedown V-symbol).

Figure 10:
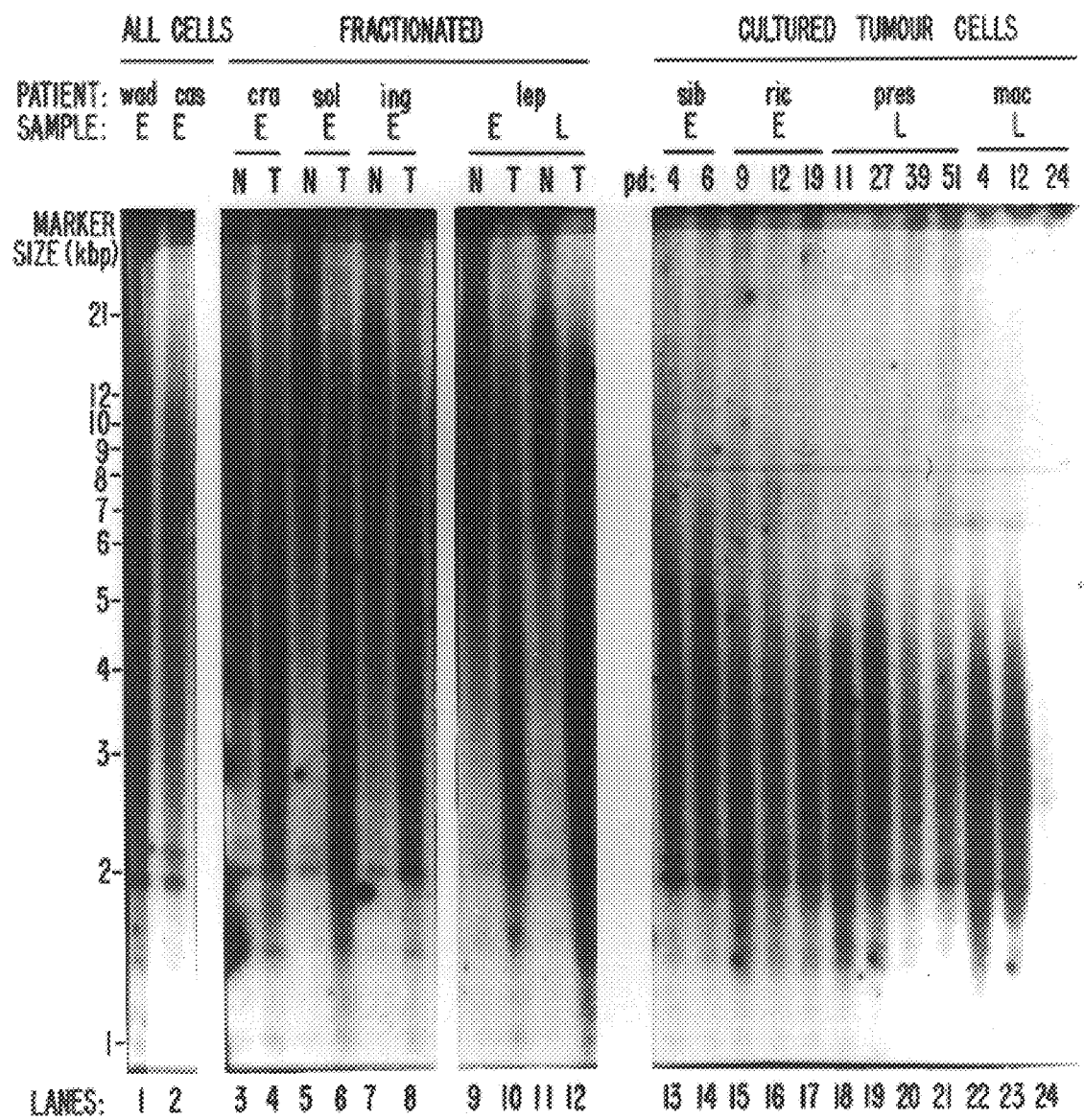

FIG. 10 is a copy of an autoradiogram showing TRF lengths of ovarian carcinoma and control normal cells. DNA from cells in ascitic fluid from 2 patients (cas and wad) was digested with HinfI and RsaI. separated by electrophoresis, hybridized to the telomeric probe $^{32}p(CCCTAA)_3$, (Seq. ID No. 4) stringently washed and autoradiographed. The cells of ascitic fluid from 7 other patients (cra, sol, ing, sib, ric, pres and mac) were separated into adhering. normal cells (N) and tumour clumps in the media (T). The DNA was extracted and run as above. DNA from patient lep was obtained from both the first and forth paracentesis. Tumour cells from patients sib, ric, pres and mac were cultured and DNA was obtained at the respected population doublings (pd).

Figure 11:
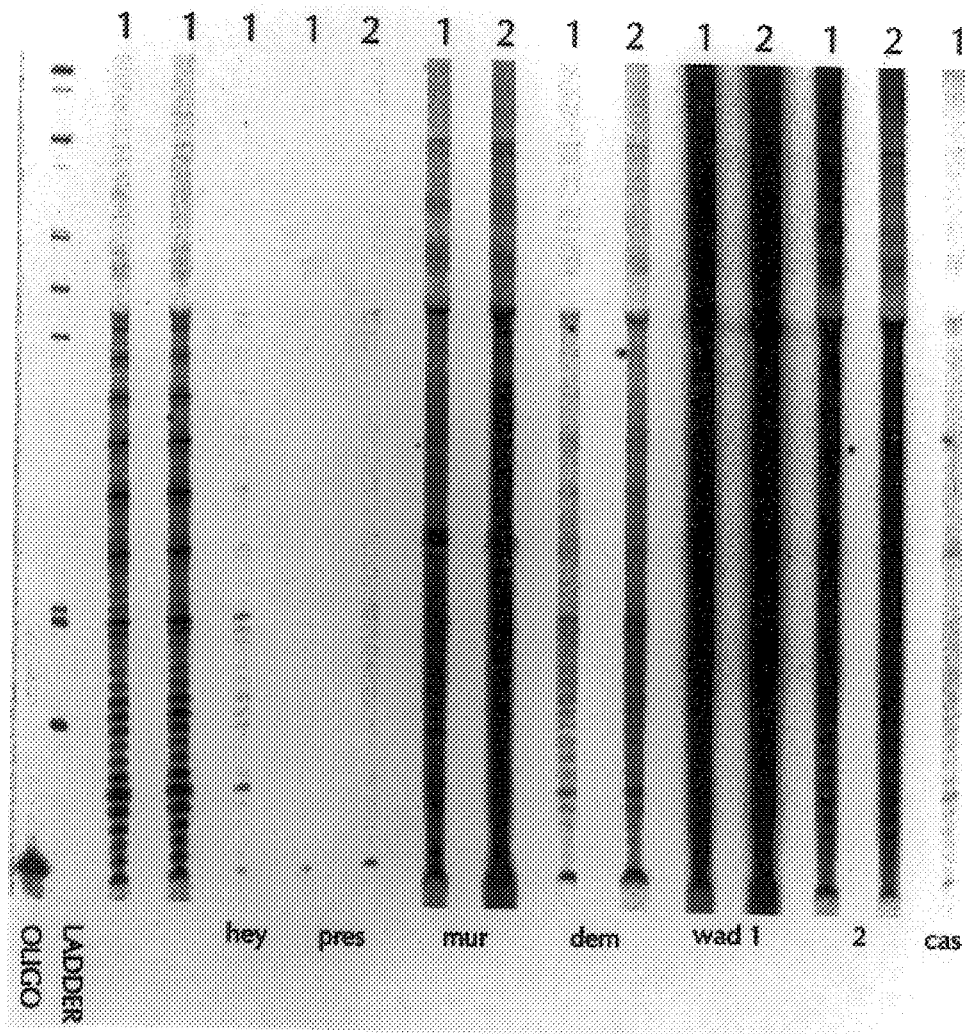

FIG. 11 shows telomerase activity in ovarian carcinoma cells. S100 extracts from control cell line 293 CSH, tumour cell line HEY, purified tumour cell population PRES and cells directly from the ascitic fluid from patients mur, dem, wad and cas were incubated with the telomere primer (TTAGGG)$_3$ (Seq. ID No. 5) in the presence of dA/TTP, $^{32}$PdGTP and buffer. The reaction products were separated on a sequencing gel and exposed to a phosphoimager screen. Either single (1) or double reactions (2) were tested.

Figure 12:
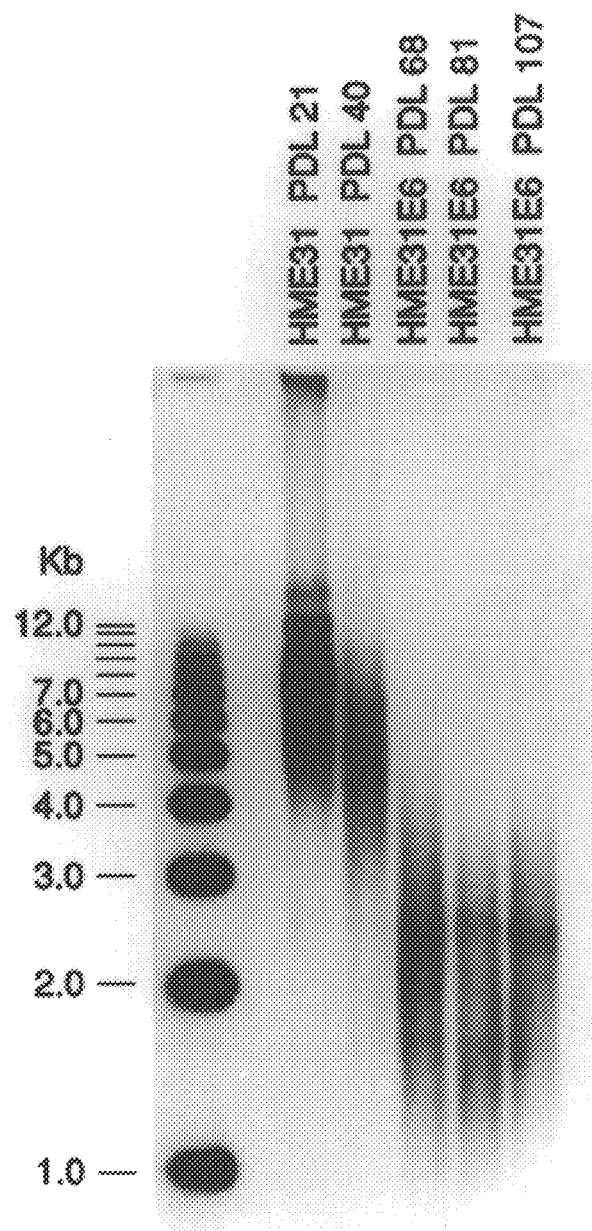

FIG. 12 is a copy of an autoradiogram showing telomere lengths in various cells.

Figure 13:
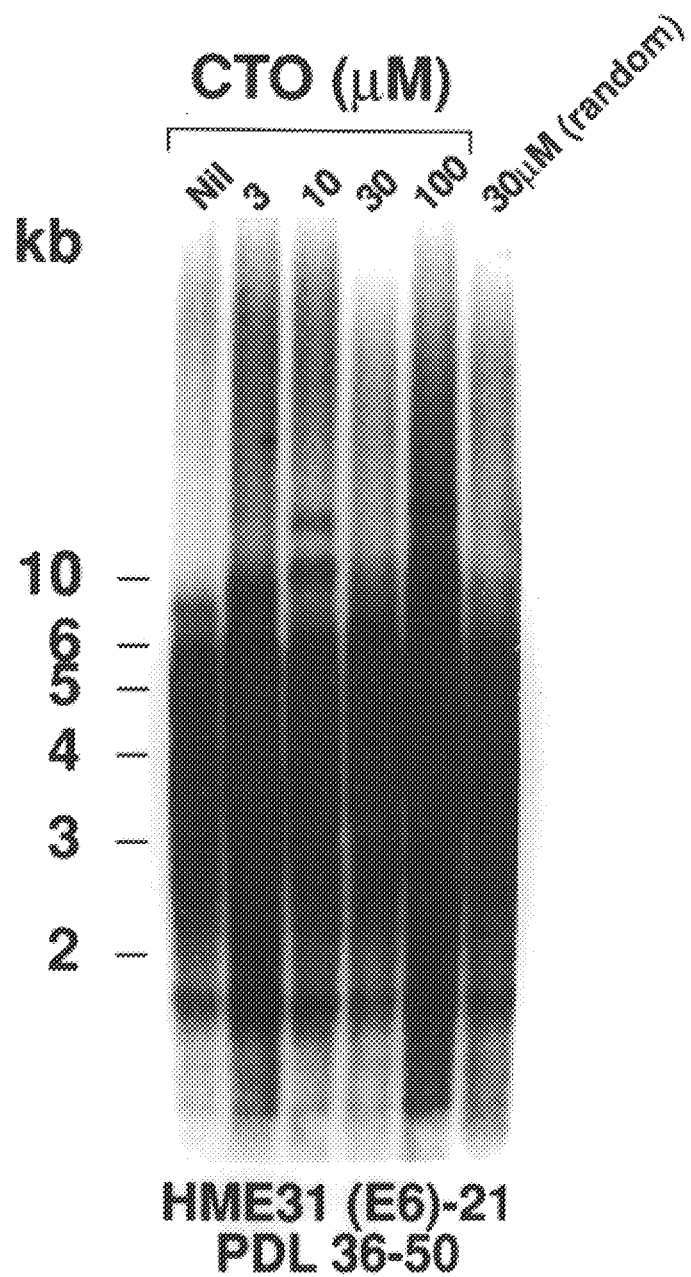

FIG. 13 is a copy of an autoradiogram showing the effect of Cytidine-rich terminal oligonucleotide (CTO) on telomere length.

Figure 14:
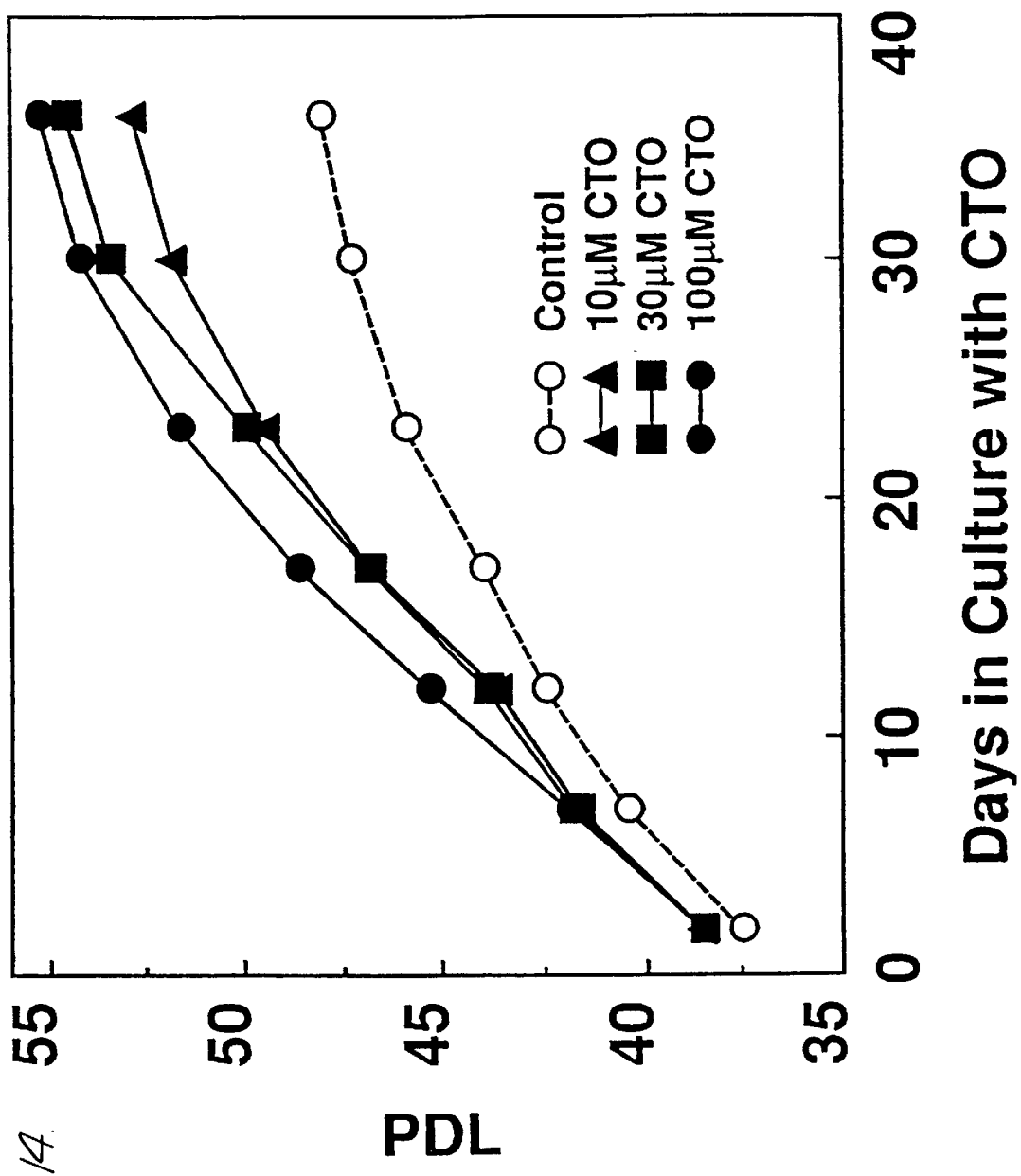

FIG. 14 is a graph showing extension of the life span of cells.

Figure 15:
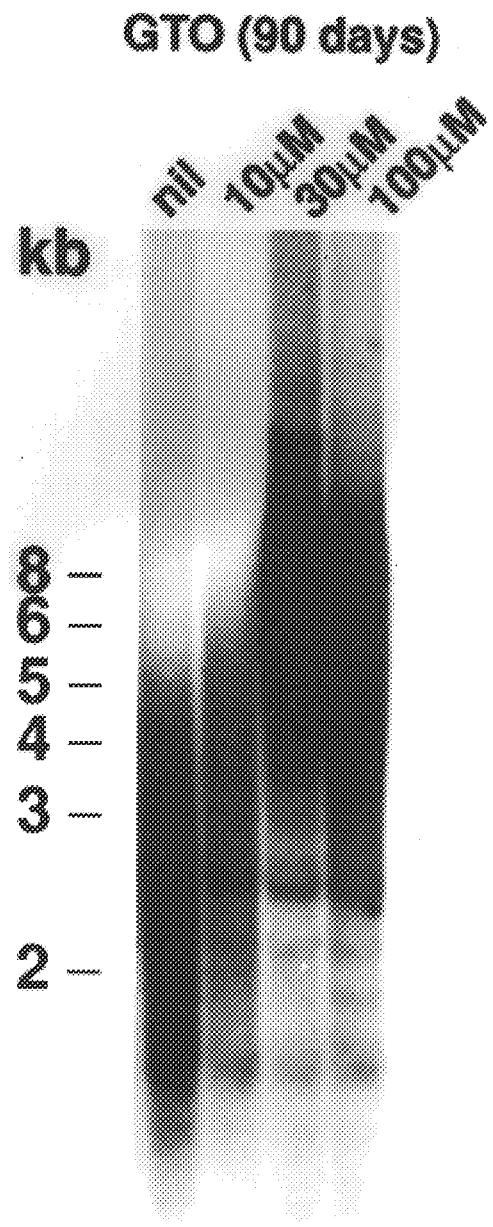
Figure 16:
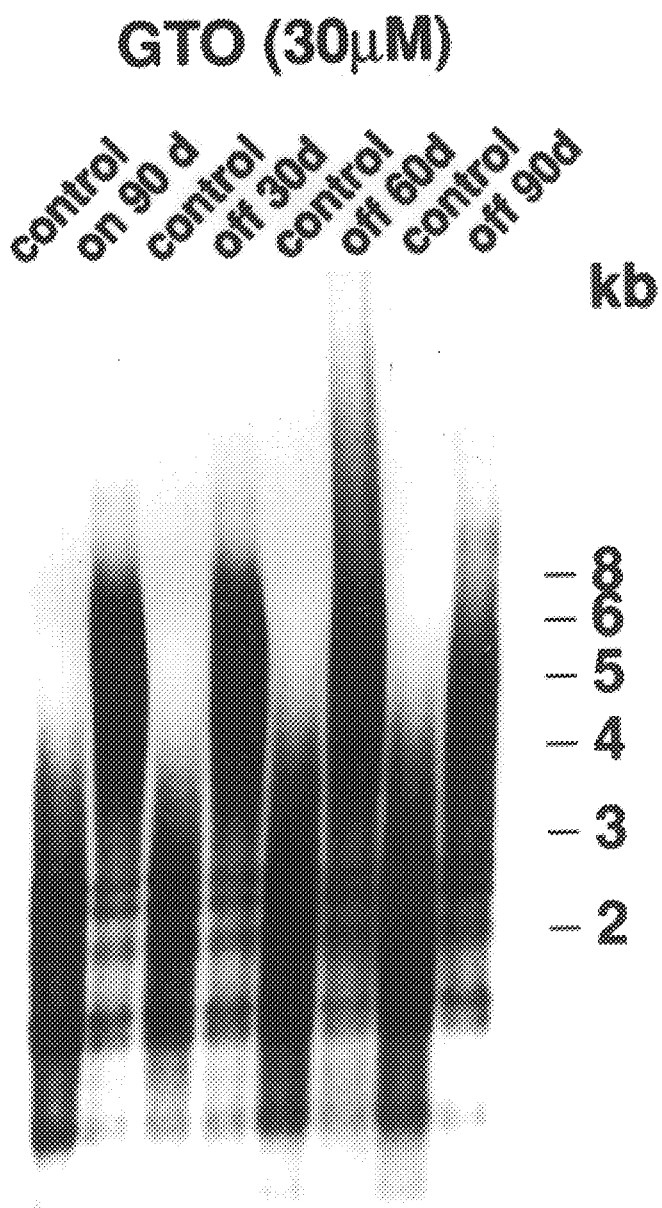

FIGS. 15 and 16 are copies of autoradiograms showing the effect of guanidine-rich terminal oligonucleotide (GTO) on telomerase activity.

TELOMERES AND TELOMERASE

All normal diploid vertebrate cells have a limited capacity to proliferate, a phenomenon that has come to be known as the Hayflick limit or replicative senescence. In human fibroblasts, this limit occurs after 50–80 population doublings, after which the cells remain in a viable but non-dividing senescent state for many months. This contrasts to the behavior of most cancer cells, which have escaped from the controls limiting their proliferative capacity and are effectively immortal.

One hypothesis to explain the cause of cellular senescence concerns the role of the distal ends of chromosomes called telomeres. The hypothesis is that somatic cells lack the ability to replicate the very ends of DNA molecules. This results in a progressive shortening of the ends of the chromosomes until some function changes, at which time the cell loses the capacity to proliferate.

DNA polymerase synthesizes DNA in a 5'→3' direction and requires a primer to initiate synthesis. Because of this, the "lagging strand" does not replicate to the very ends of linear chromosomes. The chromosome is thus shortened with every cell division. The ends of chromosomes are called telomeres, and are composed of long TTAGGG repeats. The enzyme telomerase can add TTAGGG repeats to the 3' end of the telomeric DNA, thus extending the DNA and preventing shortening.

Germline cells have long telomeres and presumably contain telomerase. Somatic cells lack telomerase activity, and their telomeres have been found to shorten with cell division both in vivo and in culture. Cancer cells are immortal, and have regained telomerase activity and thus can maintain their chromosome ends. Examples are provided below of definitive experiments which indicate that telomere shortening and telomerase activity are key factors in controlling cellular senescence.

Methods

As noted above, the present invention concerns diagnosis and therapy associated with measuring telomeric length and manipulating telomerase-dependent extension or telomerase-independent shortening. While the invention is directed to humans, it may be applied to other animals, particularly mammals, such as other primates, and domestic animals, such as equine, bovine, ovine, porcine, feline, and canine. The invention may be used in both therapy and diagnosis. In the case of therapy, for example, telomere shortening may be slowed or inhibited by providing DNA oligonucleotides or their functional equivalent, or self-proliferation can be reduced by inhibiting telomerase. In this case of diagnostics, one may detect the length of telomeres as to a particular chromosome or group of chromosomes, or the average length of telomeres. Diagnosis may also be associated with determining the activity of telomerase in cells, tissue, and the like.

Information on the relative age, remaining proliferative capacity, as well as other cellular characteristics associated with telomere and telomerase status may be obtained with a wide variety of cell types and tissues, such as embryonic cells, other stem cells, somatic cells (such as hepatocytes in the context of cirrhosis), connective tissue cells (such as fibroblasts, chondrocytes, and osteoblasts), vascular cells (such as endothelial and smooth muscle cells), cells located in the central nervous system (such as brain astrocytes), and different neoplastic tissues, where it is desirable to determine the remaining replicative capacity of the hyperplastic cells to predict growth potential.

Maintaining Telomere Length

Telomere length in cells in vitro or in vivo may be usefully maintained by a variety of procedures. These include those methods exemplified below. These examples, however, are not limiting in this invention since those in the art will recognize equivalent methods. It is expected that all the methods will be useful in manipulating telomere length now that applicant has demonstrated this experimentally. Such methods may be based upon provision of oligonucleotides or other agents which interact with telomeres to prevent shortening during cell division. In addition, the methods include treatment with agents which will include telomerase, or its equivalent activity, within a cell to prevent shortening. Finally, the methods also include modulation of gene expression associated with cell senescence.

Useful agents can be determined by routine screening procedures. For example, by screening agents which interact in an in vitro system with telomeres, and block loss of telomere ends, or aid increase in telomere length. Non-limiting examples of such methods are provided below. All that is necessary is an assay to determine whether telomere end shortening is reduced during cell division. The mechanism by which such agents act need not be known, so long as the desired outcome is achieved. However, by identifying useful target genes (e.g., the M2 mortality modulation gene(s)), antisense and equivalent procedures can be designed to more appropriately cause desired gene expression or non-expression.

In a particular example (non-limiting in this invention) one can reduce the rate of telomere shortening, by providing a nucleic acid, e.g., DNA or RNA (including modified forms), as a primer to the cells. Such nucleic acid will usually include 2 to 3 repeats, more usually 2 repeats, where the repeats are complementary to the G-rich DNA telomere strand. Such oligonucleotides may be used to extend the proliferative capability of cells.

The oligonucleotides can be transferred into the cytoplasm, either spontaneously (i.e., without specific modification) or by the use of liposomes which fuse with the cellular membrane, or are endocytosed by employing ligands which bind to surface membrane protein receptors of the cell resulting in endocytosis. Alternatively, the cells may be permeabilized to enhance transport of the oligonucleotides into the cell, without injuring the host cells. Another way is to use a DNA binding protein, e.g., HBGF-1, which is known to transport an oligonucleotide into a cell. In this manner, one may substantially reduce the rate of telomere shortening from an average of about 50 bp per division, to an average of about 6–12 bp per division (see examples below), thus significantly extending the number of divisions occurring before induced cellular senescence.

By "senescence" is meant the loss of ability of a cell to replicate in the presence of normally appropriate replicative signals, and may be associated with the expression of degradative enzymes, such as collagenase. The term does not include quiescent cells which might be induced to replicate under appropriate conditions. This term is exemplified below in the examples, where the number of cell doubling prior to senescence is increased.

The above processes are useful in vivo. As already indicated, by using liposomes, particularly where the liposome surface carries ligands specific for target cells, or the liposomes will be preferentially directed to a specific organ, one may provide for the introduction of the oligonucleotides into the target cells in vivo. For instance, utilizing lipocortin affinity for phosphatidyl serine, which is released from injured cells, the oligonucleotides may be directed to such site. Alternatively, catheters, syringes, depots or the like may be used to provide high localized concentrations. The introduction of such oligonucleotides into cells resulting in decreased senescence in response to cell division can have therapeutic effect.

The maintenance of telomere length has application in tissue culture techniques to delay the onset of cellular senescence. For instance, cell-based therapies which require the clonal expansion of cells for reintroduction into an autologous patient are limited to about 20–30 doublings. This invention allows, in the expansion of cells in the case of gene therapy, both prior to genetic manipulation and then expansion of the manipulated cells, the maintenance of telomere length. This in turn allows normal cells to be cultivated for extended doublings in vitro. Experiments described below demonstrate the utility of this method in vitro, and demonstrate its applicability in vivo.

Critical shortening of telomeres leads to a phenomenon termed "crisis" or M2 senescence. See, Shay et al., 1992, supra. Among the cells in crisis, rare mutants may become immortalized in which M2 genes have been inactivated, and where expression of telomerase is reactivated and stabilizes the telomere length. An M2 regulatory gene may be modulated to provide a useful means of modulating telomere length and telomerase activity. The repression of the M2 regulatory gene(s) by antisense or other means can provide a means of activating telomerase reversibly, such that telomeres may be extended and then telomerase again repressed. In this manner, proliferative capacity may be extended with or without the addition of oligonucleotides to slow the telomere shortening. Such cells may then be used in cell-based therapies, such as bone marrow transplantation, reconstitution of connective tissue, and transplantation of early passage adrenal cortical cells, fibroblasts, epithelial cells, and myoblasts.

Telomerase Modulation

As discussed above, cancer cells contain telomerase activity and thereby are immortal. Thus, it is useful to modulate (e.g., decrease) telomerase activity in such cells to reduce their life span. In addition, cells critical to an individual's survival, e.g., CD4$^+$ cells to an HIV-infected individual, may be immortalized by causing expression of telomerase to cause telomere shortening to be reduced or reversed.

Thus, inhibition or induction of telomerase may find application in various situations. By inhibiting telomerase intracellularly, one may reduce the ability of cancer cells to proliferate. Telomerase may be competitively inhibited by adding synthetic agents, e.g., oligonucleotides comprising 2 or more, usually not more than about 50 repeats, of the telomeric motif of the 5'-3' G-rich strand (the strand which acts as the template). The oligonucleotides may be synthesized from natural or unnatural units, e.g., the derivatives or carbon derivatives, where a phosphate-oxygen is substituted with sulfur or methylene, modified sugars, e.g., arabinose, or the like. As discussed above, other equivalent agents may also be used to inhibit or cause expression of telomerase activity.

The oligonucleotides may be introduced as described above so as to induce senescence in the immortalized cells, in culture and in vivo. Where growing cells in culture, where one wishes to prevent immortalized cells from overgrowing the culture, one may use the subject oligonucleotides to reduce the probability of such overgrowth. Thus, by maintaining the oligonucleotides in the medium, they will be taken up by the cells and inhibit telomerase activity. One may provide for linkage to the telomeric sequence with a metal chelate, which results in cleavage of nucleic acid sequences. Thus, by providing iron chelate bound to the telomeric motif, the telomerase RNA will be cleaved, so as to be non-functional.

Alternatively, one may introduce a ribozyme, having 5' and 3'-terminal sequences complementary to the telomerase RNA, so as to provide for cleavage of the RNA. In this way, the telomerase activity may be substantially inhibited, so as to result in a significant limitation of the ability of the cancer cells to proliferate. Telomerase may also be inhibited by the administration of an M2 regulator gene product. By modulating the expression of any of the proteins directly regulating telomerase expression, one may also modulate cellular telomerase activity.

The nucleic acid sequences may be introduced into the cells as described previously. Various techniques exist to allow for depots associated with tumors. Thus, the inhibiting agents or nucleic acids may be administered as drugs, since they will only be effective only in cells which include telomerase. Since for the most part, somatic cells lack telomerase activity they will be unaffected. Some care may be required to prevent entry of such drugs into germ cells, which may express telomerase activity.

The subject compositions can therefore be used in the treatment of neoplasia, as well as other proliferative diseases associated with the presence of telomerase. In addition, they can be used for studying cell senescence, the role of telomeres in the differentiation and maturation of cells from a stem cell, e.g., hematopoietic, embryonic, etc., or the like, and the role of telomerase in spermatogenesis.

Telomere Length

Procedures for measuring telomere length are known in the art and can be used in this invention. Generally, they involve specific primers of DNA synthesis of telomeres, and determination of the amount and/or extent of such DNA synthesis. Alternatively, restriction endonuclease digestion is used (with enzymes which do not cleave telomeric DNA), and the length of the fragment having detectable telomere DNA is studied. Given that the DNA sequence of a telomere is known, detection of such DNA is relatively easy by use of specific oligonucleotides. Examples of these methods are provided below.

For diagnosis, in detection of the telomeric length, one may study just a particular cell type, all cells in a tissue (where various cells may be present), or subsets of cell types, and the like. The preparation of the DNA having such telomeres may be varied, depending upon how the telomeric length is to be determined.

Conveniently, the DNA may be isolated in accordance with any conventional manner, freeing the DNA of proteins by extraction, followed by precipitation. Whole genomic DNA may then be melted by heating to at least about 80° C., usually at least about 94° C., or using high salt content with chaotropic ions, such as 6× SSC, quanidinium thiocyanate, urea, and the like. Depending upon the nature of the melting process, the medium may then be changed to a medium which allows for DNA synthesis.

(a) DNA Synthesis

In one method, a primer is used having at least about 2 repeats, preferably at least about 3 repeats of the telomeric sequence, generally not more than about 8 repeats, conveniently not more than about 6 repeats. The primer is added to the genomic DNA in the presence of only 3 of the 4 nucleotide triphosphates (having the complementary nucleosides to the protruding or G-rich strand of a telomere, e.g., A, T and C for human chromosomes), dATP, dTTP and dCTP. Usually at least the primer or at least one of the triphosphates is labeled with a detectable label, e.g., a radioisotope, which label is retained upon incorporation in the chain. If no label is used, other methods can be used to detect DNA synthesis. The primer is extended by means of a DNA polymerase, e.g., the Klenow fragment of DNA polymerase I, T7 DNA polymerase or Taq DNA polymerase The length of the extended DNA can then be determined by various techniques, e.g., those which separate synthesized DNA on the basis of its molecular weight, e.g., gel electrophoresis. The DNA synthesized may then be detected based on the label, e.g., counts incorporated per $\mu$g of DNA, where the counts will be directly proportional to telomere length. Thus, the measure of radioactivity in relation to the amount of DNA will suffice to quantitate telomere length.

If desired, telomeres of known length may be used as standards, whereby a determination of radioactivity may be read off a standard curve as related to telomere length. Instead, one may prepare tissues where individual cells may be assayed for relative telomere length by in situ hybridization. In this approach, for example, the primer is labeled with a detectable label, usually biotin or digoxygenin. Following annealing to prepared tissue sections or cells, the label is revealed histochemically, usually using autoradiography (if the label were radioactive), using avidin/streptavidin (if the label were biotin) or using antidigoxygenin antibodies (if the label were digoxygenin). The amount of signal per cell is proportional to the number of telomeric repeats, and thus to the telomere length. This can be quantitated by microfluorometry or analogous means, and compared to the signal from standard cells of known telomere length to determine the telomere length in the test sample.

(b) Restriction Endonuclease Digestion

Alternatively, one may use primers which cause covalent cross-linking of the primer to telomere DNA. In this situation, one may totally digest the DNA with restriction endonucleases which have 4 base recognition sites, which results in the production of relatively short fragments of DNA, except for telomeric DNA which lacks the recognition site. Restriction endonucleases which may find use include AluI, HinfI, MspI, RsaI, and Sau3A, where the restriction endonucleases may be used individually or in combination. After digestion of the genomic DNA, the primer may be added under hybridizing conditions, so as to bind to the protruding chain of the telomeric sequence. By providing for two moieties bound to the primer, one for covalent bonding to the telomeric sequence and the other for complex formation with a specific binding pair member, one can then provide for linking of a telomeric sequence to a surface. For example, for covalent bonding to the telomeric sequence, psoralen, or isopsoralen, may be linked to one of the nucleotides by a bond or chain and upon UV-radiation, will form a bridge between the primer and the telomere.

The specific binding pair member will normally be a hapten, which binds to an appropriate complementary member, e.g., biotin and strept/avidin, trinitrobenzoic acid and anti-trinitrobenzamide antibody, or methotrexate and dihydrofolate reductase. Rather than having the moiety for covalent bonding covalently bonded to the primer, one may add a compound into the medium which is intercalatable into the nucleic acid, so as to intercalate between double-stranded nucleic acid sequences. In this manner, one may achieve the same purpose. Use of a substantial excess of the intercalatable compound will cause it to also intercalate into other portions of DNA which are present. Various modifications of this process may be achieved, such as size separation, to reduce the amount of label containing DNA.

The specific binding pair member may be used for separation of telomeric DNA free of contaminating DNA by binding to the complementary pair member, which may be present on beads, on particles in a column, or the like. In accordance with the nature of the separation, the covalently bonded telomere strand may now be purified and measured for size or molecular weight. Again, if desired, standards may be employed for comparison of distribution values.

The specific binding pair member hapten can be present at the 5'-terminus of the primer or at intermediate nucleotides. Specifically, biotin-conjugated nucleotides are generally available and may be readily introduced into synthetic primer sequences in accordance with known ways.

The above-described techniques can also be used for isolating and identifying DNA contiguous to the telomere.

(c) Average Telomere Length

In methods of this invention it may be useful to determine average telomere length by binding a primer to a telomere prior to separation of the telomeric portion of the chromosomes from other parts of the chromosomes. This provides a double-stranded telomeric DNA comprising the telomeric overhang and the primer. A reaction may then be carried out which allows for specific identification of the telomeric DNA, as compared to the other DNA present. The reaction may involve extension of the primer with only 3 of the nucleotides (dNTPs), using a labeled nucleotide, covalent bonding of the primer to the telomeric sequence, or other methods which allow for separation of the telomeric sequence from other sequences. The length of the synthesized DNA detected then represents the average telomere length.

The determination of telomere length as described above can be associated with a variety of conditions of diagnostic interest. Following telomere length in tumor cells provides information regarding the proliferative capacity of such cells before and following administration of inhibitors of telomerase (or other treatments which destabilizes the telomere length as discussed above). It also provides a means of following the efficacy of any treatment and providing a prognosis of the course of the disease.

Where diseased tissue is involved, the native tissue can be evaluated as to proliferative capability. By "proliferative capability" is meant the inherent ability of a cell or cells in a tissue to divide for a fixed number of divisions under normal proliferation conditions. That is, the "Hayflick" number of divisions, exemplified below in the examples. Thus, despite the fact that the tissue may have a spectrum of cells of different proliferative capability, the average value will be informative of the state of the tissue generally. One may take a biopsy of the tissue and determine the average telomeric length. Using the value, one may then compare the value to average normal healthy tissue as to proliferative capability, particularly where the tissue is compared to other tissue of similar age.

In cases of cellular diseases, such as liver disease, e.g., cirrhosis, or muscle disease, e.g., muscular dystrophy, knowledge of the proliferative capability can be useful in diagnosing the likely recuperative capability of the patient. Other situations involve injury to tissue, such as in surgery, wounds, burns, and the like, where the ability of fibroblasts to regenerate the tissue will be of interest. Similarly, in the case of loss of bone, osteoarthritis, or other diseases requiring reformation of bone, renewal capability of osteoblasts and chondrocytes will be of interest.

While methods are described herein to evaluate the proliferative capacity of a tissue by taking an average measure of telomere length it is noted that the tissue may have a spectrum of cells of different proliferative capability. Indeed, many tissues, including liver, regenerate from only a small number of stem cells (less than a few percent of total cells). Therefore, it is useful in this invention to use in situ hybridization (such as with fluorescently labeled telomeric probes), to identify and quantitate such stem cells, and/or the telomeric status of such cells on an individual, rather than collective basis. This is performed by measuring the fluorescent intensity for each individual cell nucleus using, e.q., automated microscopy imaging apparatus. In addition to in situ hybridization, gel electrophoresis is useful in conjunction with autoradiography to determine not only the average telomere length in cells in a tissue sample, but also the longest telomere lengths (possibly indicating the presence of stem cells) and the size distribution of telomere lengths (which may reflect different histological cell types within a tissue, see FIGS. 10–11). Thus, the autoradiogram, or its equivalent provides useful information as to the total telomere status of a cell, or group of cells. Each segment of such information is useful in diagnostic procedures of this invention.

Telomerase Activity

Telomerase activity is of interest as a marker of growth potential, particularly as to neoplastic cells, or progenitor cells, e.g., embryonic cells. Human telomerase activity may be determined by measuring the rate of elongation of an appropriate repetitive sequence (primer), having 2 or more, usually 3 or more, repeats of the telomere unit sequence, TTAGGG. The sequence is labeled with a specific binding pair member at a convenient site, e.g., the 5'-terminus, which specific binding pair member allows for separation of extended sequences. By using one or more radioactive nucleotide triphosphates or other labeled nucleotide triphosphate, as described previously, one can measure the incorporated radioactivity as cpm per unit weight of DNA as a function of unit of time, as a measure of telomerase activity. Any other detectable signal and label may also be used, e.g., fluorescein.

The activity may be measured with cytoplasmic extracts, nuclear extracts, lysed cells, whole cells, and the like. The particular sample which is employed and the manner of pretreatment will be primarily one of convenience. The pretreatment will be carried out under conditions which avoids denaturation of the telomerase, so as to maintain the telomerase activity. The primer sequence will be selected or labeled so as to allow it to be separated from any other DNA present in the sample. Thus, a haptenic label may be used to allow ready separation of the elongated sequence, which represents the telomerase activity of the sample. The nucleotide triphosphates which may be employed may include at least one nucleotide triphosphate which is labeled. The label will usually be a radiolabel, but other labels may also be present. The labels may include specific binding pair members, where the reciprocal member may be labeled with fluorescers, enzymes, or other detectable label. Alternatively, the nucleotide triphosphates may be directly labeled with other labels, such as fluorescent labels.

The sequence elongation usually will be carried out at a convenient temperature, generally from about 20° C. to 40° C., and for a time sufficient to allow for at least about 100 bp to be added on the average to the initial sequence, generally about 30–90 minutes. After the incubation time to allow for the telomerase catalyzed elongation, the reaction may be terminated by any convenient means, such as denaturation, e.g., heating, addition of an inhibitor, rapid removal of the sequence by means of the label, and washing, or the like. The separated DNA may then be washed to remove any non-specific binding DNA, followed by a measurement of the label by any conventional means.

The determination of telomerase activity may be used in a wide variety of ways. It can be used to determine whether a cell is immortalized, e.g., when dealing with tissue associated with neoplasia. Thus, one can determine at the margins of a tumor, whether the cells have telomerase activity and may be immortalized. The presence and activity of the telomerase may also be associated with staging of cancer or other diseases. Other diagnostic interests associated with telomerase include measurement of activity as an assay for efficacy in treatment regimens designated to inhibit the enzyme.

Other techniques for measuring telomerase activity can use antibodies specific for the telomerase protein, where one may determine the amount of telomerase protein in a variety of ways. For example, one may use polyclonal antisera bound to a surface of monoclonal antibody for a first epitope bound to a surface and labeled polyclonal antisera or labeled monoclonal antibody to a second epitope dispersed in a medium, where one can detect the amount of label bound to the surface as a result of the telomerase or subunit thereof bridging between the two antibodies. Alternatively, one may provide for primers to the telomerase RNA and using reverse transcriptase and the polymerase chain reaction, determine the presence and amount of the telomerase RNA as indicative of the amount of telomerase present in the cells.

The following examples are offered by way of illustration and not by way of limitation.

EXAMPLES

The following are examples of specific aspects of the invention to merely illustrate this invention to those in the art. These examples are not limiting in the invention, but provide an indication of specific methodology useful in practice of the invention. They also provide clear indication of the utility of the invention and of the correlation between telomere length, telomerase activity and cellular senescence. Such correlation indicates to those in the art the breadth of the invention beyond these examples.

Example 1

Telomere Length and Cell Proliferation

The effects of telomere length modulation on cellular proliferation were studied. An average of 50 bp are lost per cell division in somatic cells. The telomere end is thought to have a single-stranded region as follows (although the amount of overhang is unknown):
5'TTAGGGTTAGGGTTAGGGTTAGGGT-
TAGGGTTAGGGTTAGGGTTAGGGT-
TAGGGTTAGGG
3'AATCCCAATCCC
(Seq. ID No. 1)
Applicant postulated that loss of this single-stranded overhang should be significantly slowed if cells were provided with a synthetic oligonucleotide of the sequence CCCTAACCCTAA (Seq. ID No. 2). This oligonucleotide should hybridize to the exposed single-stranded region, and serve as a primer for DNA synthesis by the normal DNA polymerase present in somatic cells. In this way, rather than shortening by an average of 50 bp per division, the telomeres may only shorten by a lesser amount per division, thus significantly extending the number of divisions required before telomere shortening induced cellular senescence. This hypothesis was tested by measuring both the change in proliferative lifespan and rate of telomere shortening in cultured cells treated with this indicated oligonucleotide, versus control oligonucleotides.

Figure 1:
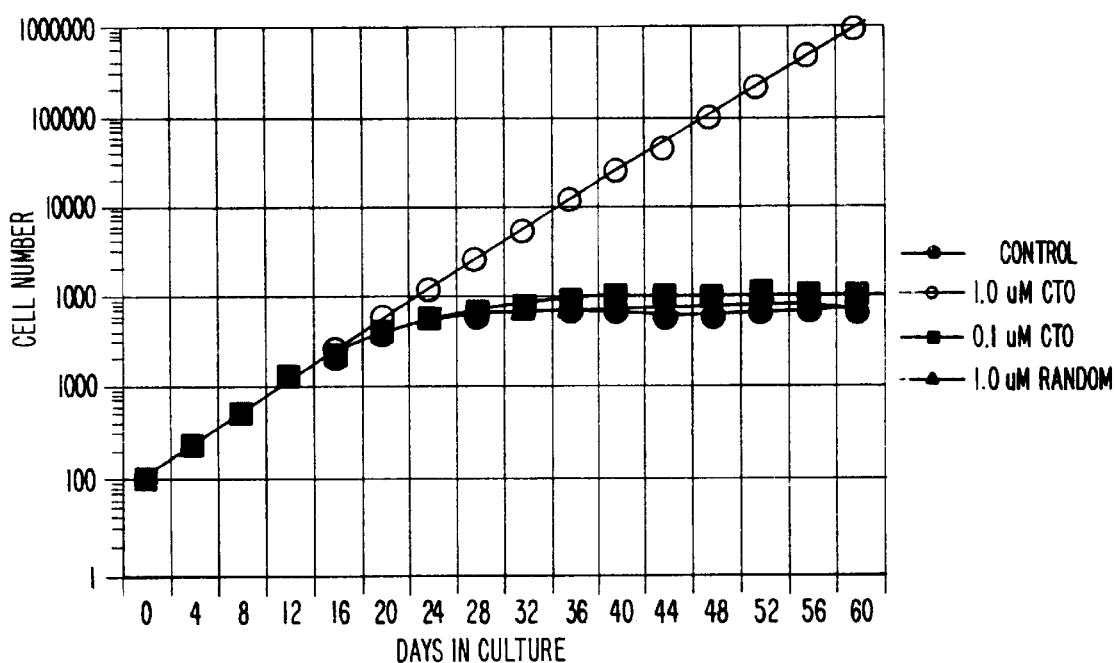
FIGS. 1–3 are graphs where the cell type and/or the culture conditions are varied, plotting days in culture (horizontal axis) length versus cell number (vertical axis).

The efficacy of the CTO-12 oligonucleotide (5'-CCCTAACCCTAA-3' Seq. ID No. 2) to reduce telomere shortening associated with cellular senescence (FIG. 1) was studied using target cells cultured under standard cell culture conditions in minimal essential medium supplemented with 10% fetal calf serum. The cells were subcultivated every four days by trypsinization upon reaching confluency and were fed new medium at subcultivation or every two days, whichever came first. Cells at various population doubling levels were seeded at 10,000 cells per well and fed medium containing oligonucleotides at various concentrations. Oligonucleotides studied were the cytidine-rich terminal oligonucleotide (CTO-12), guanidine-rich terminal oligonucleotide-12 bp (GTO-12, having the sequence 5'-TTAGGGTTAGGG-3' (Seq. ID No. 3)), and a 12 base pair randomer with a random nucleotide in every position. As an additional control, cells were fed identical medium without oligonucleotide. Cells were fed oligonucleotide every 48 hours from 10× stocks. (Such oligonucleotides may be modified to enhance stability, e.g., with phosphorothioates, dithioate and 2-O-methyl RNA.) Specifically, IMR-90 human lung fibroblasts with a proliferative capacity of approximately 55 population doublings (PD) were seeded at PD45 at 10,000 cells per well in a 48 well tissue culture dish, and fed medium only or medium supplemented with CTO-12 (at 1.0 μM and 0.1 μM) and 12 base pair randomer at 1.0 μM. As shown in FIG. 1, cells grown in medium without oligonucleotide, or with CTO-12 at less than 1.0 μM or with oligonucleotide of random sequence reached replicative senescence in a similar fashion at about 52 population doublings. Cells fed the CTO-12 oligonucleotide at 1.0 μM, however, continued to proliferate for approximately 10 doublings more than control cells.

Example 2

Inhibition of Telomerase in Cancer Cells

One way by which cancer cells are able to escape cellular senescence is by regaining telomerase activity, which permits them to maintain the length of their telomeres in the face of multiple rounds of cell division. The enzyme telomerase contains an RNA complementary to TTAGGG, which allows it to recognize the telomeres and extend them by the addition of additional TTAGGG repeats. In fact, one assay for telomerase uses a TTAGGGTTAGGG (Seq. ID No. 3) primer and measures the ability of cell extracts to synthesis a ladder of 6 bp additions to this substrate. Telomerase activity in cancer cells is likely to be present in limiting amounts since telomere length is relatively stable (thus only about 50 bp per telomere are added, so that lengthening and shortening are balanced).

Applicant hypothesized that feeding cells a synthetic TTAGGGTTAGGG oligonucleotide (Seq. ID No. 3) should competitively inhibit the ability of telomerase to elongate chromosome ends, and thus should lead to telomere shortening and senescence in cancer cells. Since somatic cells lack telomerase activity, the effects of this treatment should be strictly limited to cancer cells and the germ line.

Figure 2:
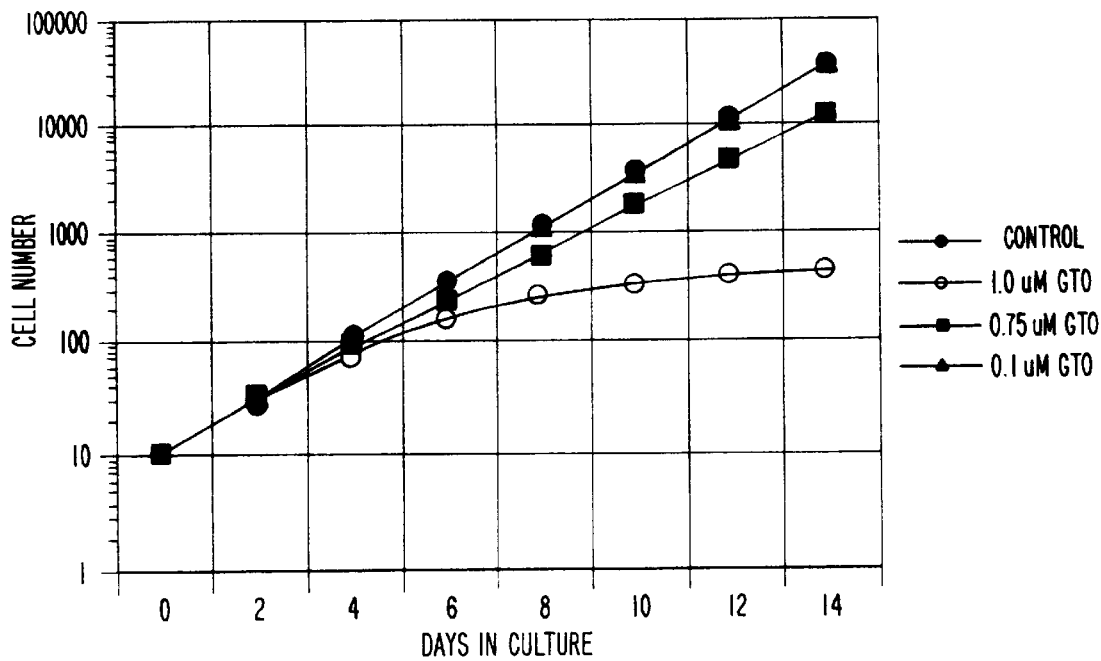
Figure 3:
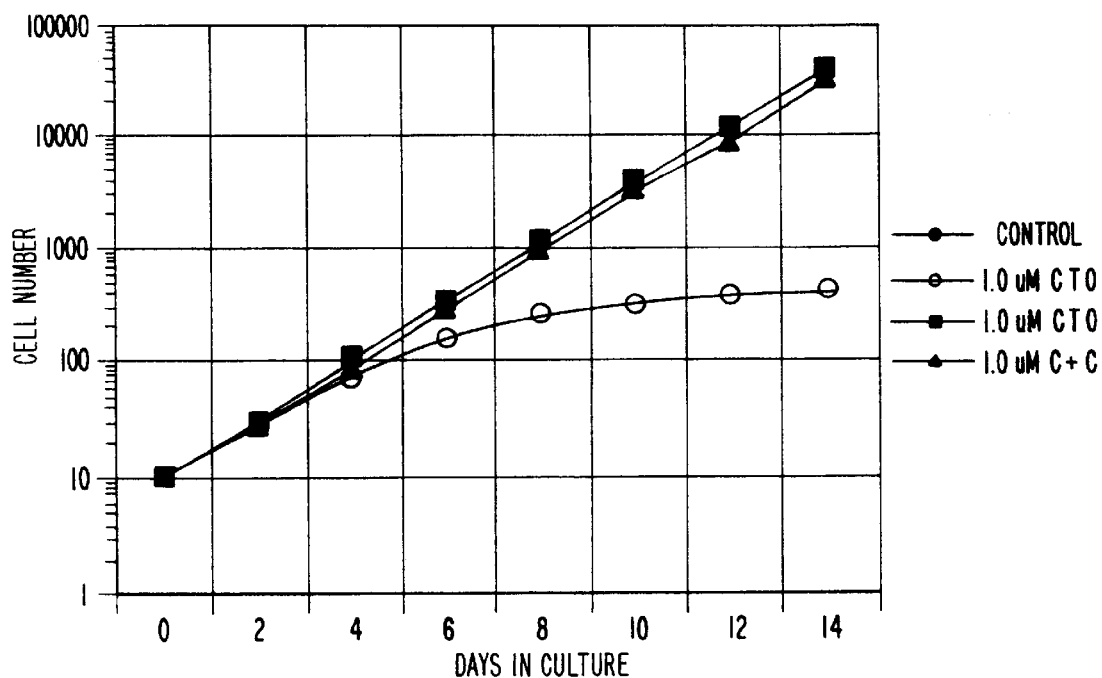

Specifically, MDA 157 human breast cancer cells with an immortal phenotype were seeded at 10,000 cells per well in 12 well tissue culture dishes and fed medium only or medium supplemented with GTO-12 (at 1.0 μM, 0.1 μM, and 0.01 μM). As shown in FIG. 2, cells grown in medium without oligonucleotide, or with doses of less than 1.0 μM continued replicating in an immortal phenotype. Cells fed the GTO-12 oligonucleotide, at 1.0 μM, however, ceased to proliferate after less than 10 doublings. Cells grown in the presence of 1.0 μM CTO-12 or 1.0 μM CTO-12 and 1.0 μM GTO-12 (G+C) continued to express the immortal phenotype suggesting that the GTO-12 oligonucleotide was not intrinsically toxic (FIG. 3). The lack of effect of the G+C mixture may reflect the CTO-12 oligonucleotide, competing with or base pairing with the GTO-12 oligonucleotide, this preventing its inhibitory effect on the cancer cell telomerase.

Example 3

Telomere Length as a Biomarker

In the U.S. and Western Europe, atherosclerosis is the principal contributor to mortality from cardiovascular diseases (Ross, 314 *N. Enql. J. Med.* 488, 1986). Atherosclerosis is characterized by the mural and focal formation of lipid and cell-rich lesions or "plaques" on the intimal surfaces of arterial tissues. This is followed by an age-dependent expansion of the lesion into the lumen, potentially leading to occlusion and to myocardial and/or cerebral infarction (Haust, (1981) in *Vascular Injury and Atherosclerosis*, ed. Moore, S. (Marcel Dekker Inc., New York), pp. 1–22; Ross and Glomset, 295(7) *N. Enql. J. Med.* 369, 1976; and Ross, 295(8) *N. Enql. J. Med.* 420, 1976). Prominent among the mechanisms proposed to explain the pathogenesis of atherosclerosis is the "response-to-injury" hypothesis (Ross, 314 *N. Enql. J. Med.* 488, 1986; Moore, (1981) in *Vascular Injury and Atherosclerosis*, ed. Moore, S. (Marcel Dekker Inc., New York), pp. 131–148; and Moore, 29(5) *Lab. Invest.* 478, 1971) in which repeated mechanical, hemodynamic and/or immunological injury to the endothelium is the initiating event.

A prediction of this hypothesis is that the intimal and medial tissue in the area comprising the atherosclerotic plaque will have a higher rate of cell turnover than the surrounding normal tissue. Several lines of evidence support this prediction. Ross et al., (Ross and Glomset, 295(7) *N. Enql. J. Med.* 369, 1976; Ross, 295(8) *N. Enql. J. Med.* 420, 1976) showed that cultured smooth muscle cells from fibrous plaques displayed lower responsiveness to growth serum when compared to cells from the underlying medial layer. Moss and Benditt 78(2) *Am. J. Pathol.* 175, 1973, showed that the replicative life-span of cell cultures from arterial plaques were equal to or less than the replicative life-spans from cells of nonplaque areas. Dartsch et al., 10 *Arteriosclerosis* 62, 1992, showed that human smooth muscle cells obtained from primary stenosing lesions became senescent in culture far later than smooth muscle cells from restenosing lesions. These results suggest that cells derived from regions of atherosclerotic plaques undergo more cellular divisions than cells from non-plaque areas hence rendering them older and nearer to their maximum replicative capacity.

Thus, to understand the pathogenesis of atherosclerosis, one must examine the alterations in the behavior of cell turnover on and adjacent to the arterial lesions. One requires a biomarker for the cell turnover of intimal and medial tissue. Several workers have examined biomarkers for the progression of atherosclerosis or for the propensity of an individual to develop atherosclerosis. The former objective entailed the measurement of a number of biochemical compounds which are detected in the plasma but originate from the endothelium. Examples are serum Type III collagen (Bonnet et al., 18 *Eur. J. Clin. Invest.* 18, 1988), von Willebrand's Factor (Factor VIII)(Baron et al., 10 *Arteriosclerosis* 1074, 1990), cholesterol, triglycerides, apolipoprotein B (Stringer and Kakkar, 4 *Eur. J. Vasc. Surg.* 513, 1990), lipoprotein (a) (Breckenridge, 143 *Can. Med. Assoc. J.* 115, 1990; Mezdour et al., 48 *Ann. Biol. Clin. (Paris)* 139, 1990; and Scanu, 14 *Clin. Cardiol.* 135, 1991), endothelin (Lerman et al., 325 *N. Enql. J. Med.* 997, 1991) and heparin-releasable Platelet Factor 4 (Sadayasu et al., 14 *Clin. Cardiol.* 725, 1991). A number of markers originate from the cell surface (Hanson et al., 11 *Arterioscler. Thromb.* 745, 1991; and Cybulsky and Girnbrone, 251 *Science* 788, 1991). Other markers monitor physiological aberrations as a result of atherogenesis (Vita et al., 81 *Circulation* 491, 1990). Candidate genes used to delineate the RFLP profile of those susceptible to atherogenesis (Sepehrnia et al., 38 *Hum. Hered.* 136, 1988; and Chamberlain and Galton, 46 *Br. Med. Bull.* 917, 1990) have also been established. However, there have been relatively few markers developed to monitor directly cell turnover.

Applicant now shows that telomere length may serve as a biomarker of cell turnover in tissues involved in atherogenesis. The results show that endothelial cells lose telomeres in vitro as a function of replicative age and that in vivo telomere loss is generally greater for tissues of the atherosclerotic plaques compared to control tissue from non-plaque regions.

In general, telomere lengths were assessed by Southern analysis of terminal restriction fragments (TRF), generated through HinfI/RsaI digestion of human genomic DNA. TRFs were resolved by gel electrophoresis and hybridized with a telomeric oligonucleotide ($^{32}$P-(CCCTAA)$_3$) (Seq. ID No. 4). Mean TRF length decreased as a function of population doublings in human endothelial cell cultures from umbilical veins (m=−190 bp/PD, P=0.01), and as a function of donor age in iliac arteries (m=−120 bp/PD, P=0.05) and iliac veins (m=−160 bp/PD, P=0.05). Thus, mean TRF length decreased with the in vitro age of all cell cultures.

When early passage cell cultures were assessed for mean TRF length as a function of donor age, there was a significant decrease for iliac arteries (m=−102 bp/y, P=0.01) but not for iliac vein (m=47 bp/y, P=0.14). Mean TRF length of medial tissue decreased significantly (P=0.05) as a function of donor age. Intimal tissues from one individual who displayed extensive development of atherosclerotic plaques possessed mean TRF lengths close to those observed for senescent cells in vitro (⁻6 kbp). These observations indicate that telomere size indeed serves as a biomarker for the replicative history of intima and media and that replicative senescence of endothelial cells is involved in atherogenesis.

Specifically, the following materials and methods were used to achieve the results noted below.

Endothelial Cell Cultures

Human umbilical vein endothelial cells (HUVEC) were obtained from Dr. Thomas Maciag of the Jerome H. Holland Laboratory of the American Red Cross. Human endothelial cells from the iliac arteries and iliac veins were obtained from the Cell Repository of the National Institute of Aging (Camden, New Jersey). Cells were grown at 37° C. in 5% $CO_2$ on 100 mm tissue plates whose interiors were treated with an overnight coating of 0.4% gelatin (37° C.). The supplemented media consisted of M199, 15% fetal bovine serum, 5 U/ml heparin and 20 μg/ml crude Endothelial Cell Growth Supplement (Collaborative Research) or crude Endothelial Cell Growth Factor (Boehringer-Mannheim). Cultures were trypsinized (0.05%, 3 minutes) at confluence, reseeded at 25% of the final cell density and refed every 2–3 days.

Tissue Samples

Tissue samples from the aortic arch, abdominal aorta, iliac artery and iliac vein were obtained from autopsies at the Department of Pathology, Health Sciences Center, McMaster University. Post-mortem times ranged from 5½ to 8½ hours. The intima was obtained by cutting open the arteries or veins and carefully scraping off the lumenal surface with a No. 10 scalpel (Lance Blades, Sheffield) (Ryan, 56 *Envir. Health Per.* 103, 1984). The resulting material was either treated directly for extraction of DNA or processed for cell culture.

The adventitial layer was removed by cutting or scraping the non-lumenal side of the vessel. The remaining medial layer was prepared for DNA extraction by freezing it in liquid-$N_2$ and grinding it in a liquid-$N_2$ chilled mortar and pestle (Kennedy et al., 158 *Exp. Cell Res.* 445, 1985). After the tissue was ground to a powder, 5 ml of frozen digestion Buffer (10 mM Tris; 100 mM NaCl; 25 mM EDTA; 0.5% SDS; pH 8.0) was added and ground into the powderized tissue. The powder was then transferred to a 50 ml Falcon tube and incubated at 48° C. until thawed. Proteinase K (10 mg/ml) was added to a final concentration of 0.2 mg/ml. After a 12–16 hour incubation, the solution was removed from the water bath and either prepared for DNA extraction or stored at 20° C.

Extraction and Restriction Enzyme Digestion of Genomic DNA

DNA was extracted as described previously (Harley et al., 345 *Nature* 458, 1990; Allsopp et al., 89 *Proc. Natl. Acad. Sci. USA* 10114, 1992). In brief, proteinase K-digested lysates were extracted twice with one volume of phenol:chloroform:isoamyl alcohol (25:24:1) and once with chloroform. Nucleic acid was precipitated by adding 2 volumes of 100% EtOH to the aqueous layer, washed once with 70% EtOH and finally resuspended in 100–200 μl of 10 mM Tris-HCl, 1 mM EDTA, pH 7.5. DNA was quantified by fluorometry and 1 μg was digested with 1 unit each of HinfI/RsaI for 3–24 hours at 37° C. Complete digestion was monitored by gel electrophoresis. The integrity of the DNA before and after digestion was monitored in control experiments by gel electrophoresis.

Southern Blot Hybridization

Electrophoresis of digested genomic DNA was performed in 0.5% agarose gels in a standard Tris, sodium borate, EDTA buffer for a total of 650–700 V/hr as described previously (Harley et al., 345 Nature 458, 1990; Allsopp et al., 89 Proc. Natl. Acad. Sci. USA 10114, 1992). After electrophoresis, the gel was placed onto 3 mm Whatman filter paper and dried under vacuum for 25 minutes at 60° C. Gels were denatured by soaking in 0.5M NaOH, 1.5M NaCl for 10 minutes at room temperature and then neutralized through immersion in 0.5M Tris, 1.5M NaCl. Genomic DNA was immersed in standard hybridization solution (Harley et al., 345 Nature 458, 1990) (6× SSC) with the telomeric $^{32}$P-(CCCTAA)$_3$ probe (Seq. ID No. 4) for 12–16 hours at 37° C. The telomeric smears were visualized through autoradiography on pre-flashed (OD$_{545}$=0.15) Kodak XAR-5 film. The mean lengths of the terminal restriction fragments (TRFs) were calculated from densitometric scans of the developed films as described previously (Harley et al., 345 Nature 458, 1990).

In vitro Results

Figure 4:
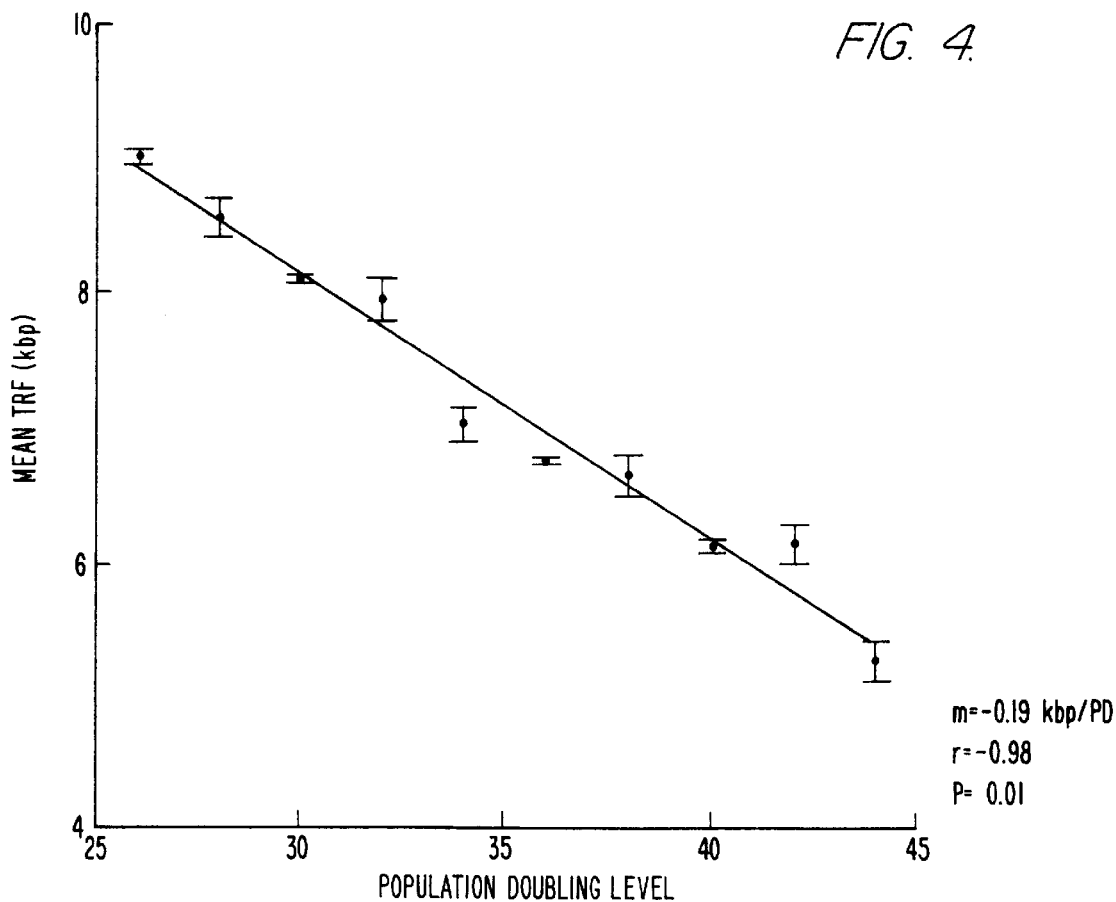
FIG. 4 is a linear plot of mean terminal restriction fragment (TRF) length versus PDL for human umbilical vein endothelial cell cultures. The plot had a slope (m) of $-190\pm10$ bp/PD, $r=-0.98$, $P=0.01$.

To determine the feasibility of employing telomere length as a biomarker for cell turnover in atherosclerosis, we first examined the change in telomere length in cultured endothelial cells where cell division can be directly monitored in vitro. The DNA was digested with HinfI and RsaI, and the resulting terminal restriction fragments (TRF) were subjected to Southern analysis. As in human skin fibroblasts (Allsopp et al., 89 Proc. Natl. Acad. Sci. USA 10114, 1992), mean TRF length decreased as a function of population doubling (PD). Thus, telomere length decreases with in vitro age of human umbilical vein endothelial cells. Mean TRF length decreased linearly (P=0.01) at a rate of 190±10 bp/PD (see FIG. 4). The Y-intercept, which signifies the mean TRF at 0 PDL is 14.0 kbp while mean TRF at senescence was 5.7±0.4 kbp.

To prove that telomere length decrease occurred in endothelial cells from other arterial and venous sources, mean TRF length versus population doubling level (PDL) was determined for several strains of endothelial cells from human iliac artery and human iliac vein. In both iliac arteries and iliac veins there was a significant (P=0.05) linear decrease in mean TRF length with age of culture: 120±60 bp per population doubling for the iliac artery and 160±30 bp per population doubling for the iliac veins from endothelial cells.

In vivo Results

Figure 5:
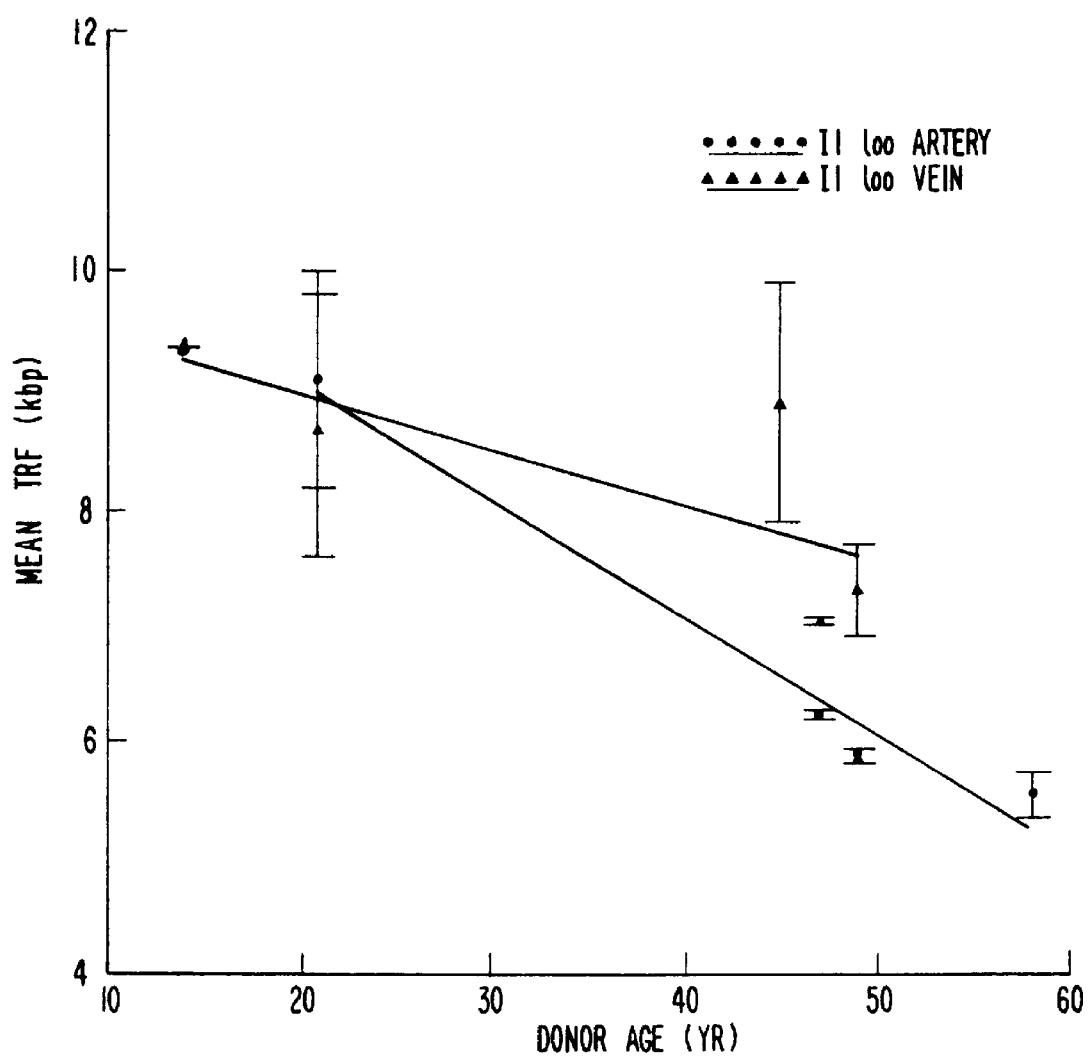
FIG. 5 is a plot of mean TRF of endothelial cell cultures from human iliac arteries and iliac veins as a function of donor age. Parameters for iliac arteries are: $m=-102$ bp/yr, $r=-0.98$, $P=0.01$ and for iliac veins are: $m=-42$ bp/yr, $r=-0.71$, $P=0.14$.

Formation of atherosclerotic plaques occurs more often in the iliac artery than in the iliac vein (Crawford, (1982) Pathology of Atherosclerosis (Butterworth and Co. Ltd., U.K.), p. 187–199), thus it is expected that turnover of intimal tissue in vivo from the iliac artery should be greater than that from the iliac veins. To test this, nine different strains of endothelial cell cultures from iliac arteries and veins of donors ranging in age from 14–58 years of age were cultivated and TRF lengths from the earliest possible PDL were determined (FIG. 5).

Consistent with the hypothesis of greater cell turnover in vivo in arteries than in veins, the rate of decrease in mean TRF length, was significant over the age range 20–60 years for iliac arteries (−100 bp/yr, P=0.01) and greater than for the iliac veins (−47 bp/yr, P=0.14). Among the nine strains of endothelial cells, there were cultures from the iliac artery and iliac vein from the same individuals for 3 of the donors, aged 21, 47 and 49 years. There was a significantly shorter mean TRF length in the cultures of iliac artery cells as compared to the venous cells for the two older donors. The younger donor showed no significant difference in mean TRF length between the two cultures, possibly reflecting relatively little difference in cell turnover between the vessels of the 21-year old donor.

Differences in mean TRF length of the cell cultures from iliac arteries and iliac veins in donors of different ages will reflect not only differences in original mean TRF length of the primary tissues but also differences in the rate of telomere loss between the different cultures in vitro during the time required to collect sufficient cells for analysis (approximately 5–10 PDL). To determine if there is a relationship between cell turnover and the extent of atherosclerotic plaque formation, we examined mean TRF length in primary tissue. Autopsies from 3, 11, 12, 14, 18, 26, 75-year old females and a 77-year old male were performed. Sections of the aortic arch, abdominal aorta, iliac artery and iliac vein were taken and the intimal and medial tissues separated and assessed for TRF length.

Sufficient intimal tissue could be obtained from the aortic arch, abdominal aorta, iliac arteries and iliac veins of 3 donors (aged 27, 75 and 77 years) for TRF analysis. There was a striking difference between the mean TRF lengths averaged over these sites in the 27-year old female (10.4±0.7 kbp) versus the 75-year old (8.8+0.6 kbp) and the 77-year old male (6.3+0.4 kbp). It is noteworthy that the 77-year old male had extensive atherosclerotic lesions in his vasculature and that the mean TRF length of his intimal tissue is close to that of endothelial cells, at senescence in vitro (approximately 6 kbp, FIG. 4).

Figure 6:
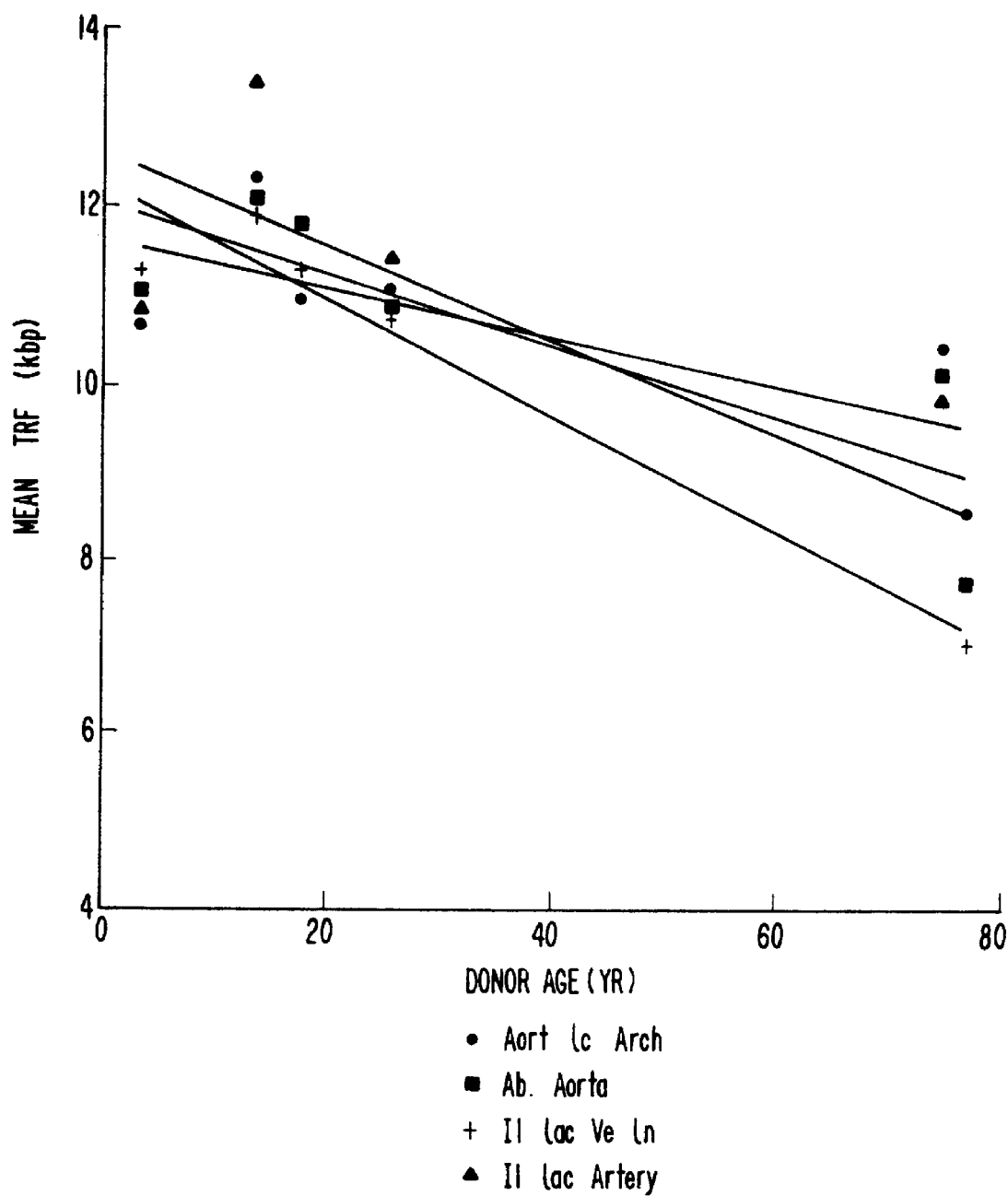
FIG. 6 is a plot of decrease in mean TRF of medial tissue from the aortic arch, abdominal aorta, iliac artery and iliac vein as a function of donor age. Parameters for linear plot are: $m=-47$ bp/yr, $r=-0.85$, $P=0.05$.

FIG. 6 shows that mean TRF of medial tissue (from the aortic arch) decreases with donor age at a small but significant rate (47 bp/yr, P=0.05). Thus, medial cells turnover in vivo occurs at a rate less than that of the venous or arterial endothelial cells.

In general, telomere loss in medial tissue underlying an atherosclerotic plaque was greater than those in non-plaque regions (Table 1). With the 75-year old female, mean TRF was significantly reduced in medial DNA from the plaque regions versus the non-plaque regions of both the aortic arch (P=0.04) and the abdominal aorta (P=0.01). For the 77-year old male, this was observed in the abdominal aorta (P=0.01).

TABLE 1

Mean TRF values for primary medial tissues of plaque and non-plaque areas

| | Plaque Region | Non-Plaque Region | P |
|---|---|---|---|
| 75-year old Donor | | | |
| Aortic Arch | 10.2 ± 0.5 | 11.1 ± 0.1 | 0.04 |
| Abdominal Aorta | 9.5 ± 0.6 | 11.0 ± 0.1 | 0.01 |

TABLE 1-continued

Mean TRF values for primary medial tissues of plaque and non-plaque areas

|  | Plaque Region | Non-Plaque Region | P |
|---|---|---|---|
| 77-year old Donor |  |  |  |
| Aortic Arch | 8.2 ± 0.4 | 8.4 ± 0.2 | NS |
| Abdominal Aorta | 7.1 ± 0.1 | 8.2 ± 0.4 | 0.01 |

These results show that mean TRF length decreases as a function of donor age for primary medial and intimal tissue, suggesting that cell turnover does occur in cardiovascular tissue. The decrease in mean TRF length for plaque regions versus clear regions of medial tissue from the same blood vessel is consistent with augmented cell turnover of tissue associated with atherosclerotic plaques. Thus, the results indicate that measurement of telomere length provides a biomarker for alterations of cellular turnover in tissues associated with cardiovascular diseases, i.e., cells of the intima and media.

Measurement of telomere length is a direct register of proliferative history but to obtain telomeric DNA one must obtain a biopsy of endothelial tissue. Since removal of the endothelium in itself can induce plaque formation, the biopsy strategy obviously entails ethical and practical problems. Based upon experience with autopsy samples one requires a minimal area of 1 cm² in order to perform a Southern analysis as described in this paper. For a practical biopsy, this is untenable. A detection technique to circumvent this problem may be confocal fluorescent microscopy. In situ hybridization to genomic DNA would require 50 times less material.

Example 4

Simplified Test for Telomere Length

Telomere length has been found to be the best predictor of the remaining lifespan of cells cultured from donors of different ages. The ability to measure telomere length thus has significant clinical use. Because of their simple repetitive nature, telomeres lack DNA sequences recognized by many restriction enzymes. One way to measure telomere length is to digest DNA with restriction enzymes with 4-base recognition sites, which cuts most of the DNA into very small pieces and leaves the telomeres in relative large TRFs (Terminal Restriction Fragments). A Southern blot of the DNA is then probed with a radioactive TTAGGGT-TAGGGTTAGGG (Seq. ID No. 5) oligonucleotide, and the size of the TRF determined.

A much simpler method to measure telomere length exploits the fact that the telomere sequence lacks guanidine residues in the C-rich strand. Genomic DNA can be melted and mixed with the DNA synthesis primer CCCTAAC-CCTAACCCTAACCCTAA (Seq. ID No. 6) in the presence of DNA polymerase and only three deoxynucleotides (dATP, dTTP and radioactive dCTP). Rare complementary sequences scattered throughout the genome would fail to extend due to the lack of dGTP. The length of the extended DNA can then be determined from a simple gel electrophoresis. The amount of DNA synthesized (counts incorporated per $\mu$g of DNA) will be directly proportional to telomere length, and for diagnostic purposes a simple measure of radioactivity would then suffice to quantitate telomere length.

Example 5

Identification of DNA Sequences Near Telomeres

There are good reasons to believe that the regulatory factors that control cellular and organismal senescence are located near telomeres, and are themselves regulated by the length of the adjacent telomere. It is thus important to identify and clone them in order to be able to understand and manipulate the aging process. In addition, there is great interest in identifying unique telomeric DNA within the human genome project, since telomeric markers for mapping purposes are lacking for the ends of the chromosomes.

In one method, large telomeric DNA is purified as follows. A biotinylated CCCATTCCCATTT (Seq. ID No. 7) oligonucleotide is used to prime DNA synthesis in double-stranded genomic DNA. The only sequences with which this oligonucleotide can anneal will be the single-stranded. base overhangs at telomere ends. The extended DNA will then be digested with a restriction enzyme such as NotI to produce large restriction fragments. Biotinylated fragments are retrieved using streptavidin coated magnetic beads, and analyzed by pulsed field electrophoresis. 46 fragments (one for each end of the 23 human chromosomes) are produced.

Multiple strategies can be used to pursue the successful isolation of large telomeric DNA. The DNA can be labeled and used to screen cDNA libraries in order to identify genes located near telomeres. The expression of these cDNAs can then be examined in young versus old cells in order to identify those which are differentially expressed as a function of cellular senescence, and which are thus candidates to be regulatory factors that control aging.

The purified telomeric DNA can also be digested with additional restriction enzymes, mixed with 100-fold excess of genomic DNA, melted and reannealed. Under these circumstances, the repetitive sequences in the telomeric DNA will anneal with genomic DNA while unique sequences in the purified DNA will self-anneal. Only the self-annealed unique sequences will contain restriction overhangs at each end, and thus a simple cloning of the annealed DNA will result in the successful cloning of only unique fragments.

Example 6

Telomere Loss in Down's Syndrome Patients

Loss of telomeric DNA from human chromosomes may ultimately cause cell cycle exit during replicative senescence. Since lymphocytes have a limited replicative capacity and blood cells were previously shown to lose telomeric DNA during aging in vivo, we wished to determine whether accelerated telomere loss is associated with the premature immunosenescence of lymphocytes in individuals with Down's Syndrome (DS), and whether telomeric DNA is also lost during aging of lymphocytes in vitro.

To investigate the effects of aging and trisomy 21 on telomere loss in vivo, genomic DNA was isolated from peripheral blood lymphocytes of 140 individuals (0–107 y) and 21 DS patients (0–45 y). Digestion with restriction enzymes HinfI and RsaI generated terminal restriction fragments (TRFs) which can be detected by Southern analysis using a telomere-specific probe, ($^{32}$P-(CCCTAA)$_3$)(Seq.ID No. 4). The rate of telomere loss was calculated from the decrease in mean TRF length as a function of donor age. DS patients showed a significantly higher rate of telomere loss with donor age (133±15 bp/y) compared to age-matched controls (41±7.7 bp/y) (P<0.0005), indicating that accelerated telomere loss is a biomarker of premature immunosenescence of DS patients, and may play a role in this process.

Telomere loss during aging in vitro was calculated for lymphocytes from two normal individuals grown in culture for 20–30 population doublings. The rate of telomere loss was 90 bp/cell doubling, that is, it was comparable to that seen in other somatic cells. Telomere lengths of lymphocytes from centenarians and from older DS patients were similar to those of senescent lymphocytes in culture, which suggests that replicative senescence could partially account for aging of the immune system in DS patients and elderly individuals.

The following materials and methods were used to obtain the results provided below.

Culture of Human Peripheral Blood T LvmDhocytes

Adult peripheral blood samples were collected, and mononuclear cells were isolated by Ficoll-Hypaque gradient centrifugation then cryopreserved in liquid nitrogen. Cultures were initiated by mixing $10^{-6}$ mononuclear cells with $10^6$ irradiated (8000 Rad) lymphoblastoid cells (Epstein-Barr virus transformed B cells), or $10^6$ mononuclear cells with 10 μg/ml phytohemagglutinin (PHA-P, Difco) in each well of a 48-well cluster plate (Costar). After 8 to 11 days, cells were washed and plated in 2 ml wells of 24-well cluster plates at a concentration of $2-4\times10^5$/ml. Cultures were passaged every three to four days, or whenever viable cell concentration (determined by trypan blue exclusion) reached $>8\times10^5$/ml. Cultures were terminated when they showed no proliferative response to irradiated lymphoblastoid cells and/or when there were no viable cells present in the entire visual field of the haemocytometer. Once transferred to the 2 ml wells, cells were continuously exposed to 25 U/ml of recombinant interleukin-2 (Amgen). The media used were (a) RPM1 (Irvine Scientific) supplemented with 10 to 20% fetal calf serum, 2 mM glutamine, and 1 mM Hepes; (b) AIM V™, a DMEM/nutrient mixture F-12 basal medium, containing purified human albumin, transferring, and recombinant insulin (Gibco), supplemented with 25% Ex-cyte (an aqueous mixture of lipoprotein, cholesterol, phospholipids, and fatty acids, (Miles Diagnostics).

At each cell passage, the number of population doublings (PD) was calculated according to the formula: PD=1n (final viable cell no. 1initial cell no.)/1n2.

Isolation of DNA

PBLs (including=15% monocytes) were isolated using Ficoll-Hypaque gradient centrifugation (Boyum et al., 21(97) Scan. J. Clin. Lab. Invest. 77, 1968) and washed 3 times in PBS. Cell pellets were resuspended in 500 μl of proteinase K digestion buffer (100 mM NaCl, 10 mM Tris pH 8, 5 mM EDTA, 0.5% SDS) containing 0.1 mg/ml proteinase K and incubated at 48° C. overnight. Lysates were extracted twice with phenol/chloroform/isoamyl alcohol (25:24:1 v/v/v) and once with chloroform. DNA was precipitated with 95% ethanol and dissolved in TE (10 mM Tris, 1 mM EDTA, pH=8).

Analysis of Telomeric DNA

Genomic DNA (10 μg) was digested with HinfI and RsaI (BRL) (20 U each), re-extracted as above, precipitated with 95% ethanol, washed with 70% ethanol, dissolved in 50 μl TE, and quantified by fluorometry. One μg of digested DNA was resolved by electrophoresis in 0.5% (w/v) agarose gels poured on Gel Bound (FMC Bioproducts) for 700 V-h. Gels were dried at 60° C. for 30 minutes, denatured, neutralized, and probed with 5' end-labeled $^{32}$P-(CCCTAA) as described above. Autoradiograms exposed within the linear range of signal response were scanned with a Hoefer densitometer. The signal was digitized and subdivided into 1 kbp intervals from 2 kbp to 21 kbp for calculation of the mean TRF length (L) using the formula $L=\Sigma(OD_i-L_i)/\Sigma OD_i$, where $OD_i$= integrated signal in interval i, and L=TRF length at the mid-point of interval i.

TRF Length vs. Age

When measured as a function of donor age, mean TRF length in PBS of 140 unrelated normal individuals (aged 0–107 y) declined at a rate of 41±2.6 bp/y (p<0.00005, r=0.83). This rate of TRF loss for PBLs is close to that previously found for peripheral blood cells by Hastie et al., 346 Nature 866, 1990. When our data were separated according to gender it was noticed that males lost telomeric DNA at a rate slightly faster than that of females (50±4.2 vs 40±3.6 bp/y), but this difference did not reach statistical significance (p=0.1). The 18 centenarians (aged 99–107 y) among our population of normal individuals had a mean TRF length of 5.28±0.4 kbp (FIG. 7). Interestingly, the standard deviation of mean TRF values for the centenarians (0.4 kbp) was much smaller than that of other age groups. Although it is possible that this represents selection of a more homogeneous population of cells with age, it is also possible that the group of centenarians were less genetically diverse than the younger populations in our study.

Mean TRF length was also analyzed in PBLs of 21 Down's Syndrome individuals (aged 2–45 y) and the rate of loss was compared to 68 age-matched controls (aged 0–43 y). We found that cells from DS patients showed a significantly greater rate of telomere loss (133±15 bp/y vs 41±7.7 bp/y; one tailed t-test, t=5.71, p<0.0005) (FIG. 8).

To determine the rate of telomere loss as a function of cell doublings, we cultured normal lymphocytes from 2 individuals in vitro until replicative senescence and measured mean TRF length at several population doubling levels (FIG. 9). Mean TRF length decreased 90 bp/population doublings in these strains, within the range observed for other human somatic cell types. The mean TRF length at senescence for the lymphocyte cell strains shown here and one other analyzed at terminal passage (FIG. 9), was 5.1±0.35 kbp. The observed TRF values in vivo for PBLs of centenarians (5.3±0.4 kbp) and old DS patients (4.89±0.59 kbp), were close to this value, suggesting that a fraction of the cells from these individuals were close to the limit of their replicative capacity.

The results showing that telomeres in PBLs from normal individuals shorten during aging in vivo and in vitro extend similar observations on human fibroblasts (Harley et al., 345 Nature 458, 1990) and support the hypothesis that telomere loss is involved in replicative senescence. We also found that in Down's Syndrome, the rate of telomere loss in PBLS in vivo was significantly higher than that in age-matched normal donors. Thus, accelerated telomere loss in PBLS of trisomy 21, a syndrome characterized by premature immunosenescence and other features of accelerated aging (Martin, "Genetic Syndromes in Man with Potential Relevance to the Pathobiology of Aging", in: Genetic Effects on Aging, Bergsma, D. and Harrison D. E. (eds.), pp. 5–39, Birth Defects: Original article series, no. 14, New York: Alan R. Liss (1978)), could reflect early senescence of lymphocytes.

The increased rate of telomere loss in PBS from DS patients could reflect a higher turnover rate of cells in vivo due to reduced viability of the trisomy 21 cells. However, it is also possible that the rate of telomere loss in PBLS from DS patients is greater per cell doubling than that in normal individuals.

The pathology of DS is similar in many ways to normal aging. Premature senescence of the immune system possibly plays a role in this similarity since DS patients have a high incidence of cancer and suffer from autoimmunity. In support of this idea, lymphocytes of older DS patients and old individuals share several characteristics, including diminished response of T-cells to activate and proliferate in response to antigen, low replicative capacity, and reduced B- and T-cell counts (Franceschi et al., 621 Ann. NY Acad. Sci. 428, 1991). Our finding that telomere length decreased faster in DS patients than normal individuals, and that the mean TRF length in centenarians and old DS patients in vivo were similar to that of senescent lymphocytes in vitro (=5 kbp)1 extends these observations. Moreover, these data suggest that replicative senescence within the lymphoid lineage in vivo contributes to the compromised immune system of both elderly individuals and Down's Syndrome patients.

Example 7

Ovarian Cancer and Telomerase Activity

The following is an example of a method by which telomerase activity is shown to correlate with the presence of cancer cells. In addition, the length of TRF was determined as an indication of the presence of tumor cells. Generally, it was found that tumor cells had significantly lower TRF values than surrounding normal cells, and had telomerase activity. Thus, these two features are markers for the presence of tumor cells.

The following methods were used to obtain these results:

Separation of Tumor and Non-tumor Cells

In one method, ascitic fluid was obtained by either diagnostic laparotomy or therapeutic paracentesis (from patients diagnosed as having ovarian carcinoma), and centrifuged at 600 ×g for 10 minutes at 4° C. The cell pellet was washed twice in 10 to 30 ml of phosphate buffered saline (PBS: 2.7 mM KCl, 1.5 mM $KH_2PO_4$, 137 mM NaCl and 8 mM $Na_2HPO_4$) and centrifuged at 570 ×g for 4 minutes at 4° C. After the final wash the cell pellet was resuspended in 20 ml of PBS and filtered through a 30 or 10 μm nylon mesh filter (Spectrum) which retains the tumor clumps but not single cells. The filters were backwashed to liberate highly purified tumor clumps. The flow-through was a combination of fibroblasts, lymphocytes and tumor cells.

In another method ascitic fluid cells were collected and washed as described above. The cellular pellet was resuspended in α-MEM with 10% fetal calf serum and cultured in 150 mm dishes. After 12 hours the media was removed and new plates were used to separate the adhering fibroblasts from the nan-adhering cells in the medium. After 12 hours the media containing mostly tumor clumps was removed from the second plates and allowed to adhere in DMA F12 medium supplemented with 3% fetal calf serum, 5 ng/ml EGF, 5 μg/ml insulin, 10 μg/ml human transferring, $5\times10^-$sM phosphoethanolamine and $5\times10^{-5}$M ethanolamine. These tumor cells were cultured for DNA analysis and S100 extracts.

DNA Extraction

Cells were lysed and proteins were digested in 10 mM Tris-HCl (pH 8.0), 100 mM NaCl, 25 mM EDTA, 0.5% SDS, 0.1 mg/ml proteinase K at 48° C. overnight. Following 2 extractions with phenol and 1 with chloroform, DNA was precipitated with ethanol and dissolved in 10 mM Tris-HCl (pH 8.0), 1 mM EDTA (TE).

Determination of TRF Length and Amount of Telomeric DNA

Genomic DNA was digested with HinfI and RsaI, extracted and precipitated as above, and redissolved in TE. DNA concentration was measured by fluorometry (Morgan et al., 7 Nucleic Acids Res. 547, 1979). DNA samples (1 μg each) were loaded onto a 0.5% agarose gel and electrophoresed for 13 hours at 90 V. The gel was dried at 60° C. for 30 minutes, denatured in 1.5M NaCl and 0.5M NaOH for 15 minutes, neutralized in 1.5M NaCl, 0.5M Tris-HCl (pH 8.0) for 10 minutes and hybridized to a $5'^{32}P(CCCTAA)_3$ telomeric probe in 5× SSC (750 mM NaCl and 75 mM sodium citrate), 5× Denhart's solution (Maniatis et al., Molecular Cloning: A Laboratory Manual, Cold Spring Harbor Laboratory, Cold Spring Harbor (1982)) and 0.× P wash (0.5 mM pyrophosphate, 10 mM $Na_2HPO_4$) at 37° C. for 12 hours. Following three high stringency washes in 0.24× SSC at 20°–22° C. (7 minutes each), the gel was autoradiographed on pre-flashed (OD=0.15) Kodak XAR-5 X-ray films for 3 days with enhancing screens. Each lane was scanned with a densitometer and the data used to determine the amount of telomeric DNA and the mean TRF length as previously described (Harley et al., 345 Nature 458, 1990).

Preparations of S-100 Cell Extracts

A minimum of $6\times10^8$ cells were used for each extract. Ascitic fluid or purified ascitic fluid tumor cells (by the first method described above) were centrifuged at 570 ×g for 4 minutes at 4° C. Ascitic fluid tumor cells separated by the second method described above (grown in monolayer) were harvested by scraping with a rubber policeman, and centrifuged as above. The pellets were rinsed twice in cold PBS followed by centrifugation as above. The final pellet was rinsed in cold 2.3× Hypo buffer (1× Hypo buffer: 10 mM Hepes (pH 8.0)), 3 mM KCl, 1 mM $MgCl_2$, 1 mM DTT, 0.1 mM PMSF and 10 U/ml of RNAsin, 1 μM leupeptin and 10 μM pepstatin A, centrifuged for 5 minutes and resuspended in 0.75 volumes of 2.3× Hypo buffer. After incubation on ice for 10 minutes the sample was transferred to an ice cold 7 or 1 ml Dounce homogenizer and homogenized on ice using a B pestle (25–55 μm clearance). After a further 30 minutes on ice the samples having a volume larger than 1 ml were centrifuged for 10 minutes at 10,000 rpm (16,000 ×g) at 4° C. in a Beckman J3-13.1 swinging bucket rotor. One-fiftieth volume of 5M NaCl was added, and the supernatants were centrifuged for 1 hour at 38,000 rpm (100,000 ×g) at 4° C. in a Beckman Ti50 rotor. Glycerol was added to a final concentration of 20% and the extract aliquoted and stored at −70° C. Samples less than 1 ml were centrifuged at 55,000 rpm for 1 hour at 4° C. in a TLA 100.2 rotor (Beckman) and NaCl and glycerol were added to the supernatant as above. Protein concentration in a typical extract was approximately 4 mg/ml.

Telomerase Assay

Telomerase activity was assayed by a modification of the method of Morin, 59 Cell 521, 1989. Aliquots (20 μl) of S-100 cell extract were diluted to a final volume of 40 μl containing 2 mM dATP, 2 mM dTTP, 1 mM $MgCl_2$, 1 μM $(TTAGGG)_3$ (Seq. ID No. 5) primer, 3.13 μM (50 μCi) α-$^{32}$P-dGTP (400 Ci/mmole), 1 mM spermidine, 5 mM β-mercaptoethanol, 50 mM potassium acetate, and 50 mM Tris-acetate (pH 8.5). In some experiments reaction volumes were doubled. The reactions were incubated for 60 minutes at 30° C. and stopped by addition of 50 μl of 20 mM EDTA and 10 mM Tris-HCl (pH 7.5) containing 0.1 mg/ml RNAseA, followed by incubation for 15 minutes at 37° C. To eliminate proteins, 50 μl of 0.3 mg/ml Proteinase K in 10 mM Tris-HCl (pH 7.5), 0.5% SDS was added for 10 minutes at 37° C. Following extraction with phenol and chloroform, unincorporated α-$^{32}$P-dGTP was separated by centrifuging the samples for 4 minutes at 500 g in a swinging bucket rotor through NICK SPIN columns (Pharmacia). DNA was precipitated by the addition of 5.3 μl of 4M NaCl, 4 μg of carrier tRNA and 500 μl of ethanol at −20° C. DNA pellets were resuspended in 3 μl of formamide loading dye, boiled for 1 minute, chilled on ice and loaded onto an 8% polyacrylamide, 7M urea sequencing gel and run at 1700 V for 2 hours using 0.6× TBE buffer. Dried gels were exposed to Kodak XAR-5 pre-flashed film at −70° C. with enhancing screen or to phosphoimager screens (Molecular Dynamics) for 7 days.

The results of the above experiments are shown in tables 2 and 3 below:

TABLE 2

Characteristics of ATCC Ovarian Carcinoma Cell Lines

| Cell line | Mean TRF Length (kbp) | Telomerase Activity |
| --- | --- | --- |
| HEY | stable at 3.7 | + |
| CAOV-3 | stable at 3.7 | N.D. |
| SKOV-3 | Increases at 60 bp/pd | N.D. |

TABLE 3

Characteristics of Ovarian Carcinoma Tumor Cells from Ascitic Fluid

| Patient | Description | Mean TRF Length (kbp) | Telomerase Activity |
| --- | --- | --- | --- |
| Pres-3 | Purified tumor cells | 3.7 | + |
| Mac-2 | Purified tumor cells | 3.7 | N.D. |
| Sib-1 | Purified tumor cells | 4.2 | N.D. |
| Ric 207 | Purified tumor cells | 3.3 | N.D. |
| Cra-1 | Purified tumor cells | 5.2 | N.D. |
| Ing-1 | Purified tumor cells | 5.8 | N.D. |
| Lep-1 | Purified tumor cells | 5.8 | N.D. |
| Lep-4 | Purified tumor cells | 5.6 | N.D. |
| Sol-1 | Purified tumor cells | 5.6 | N.D. |
| Rud-1 | Ascitic fluid cells | 3.4 | + |
| Murr-1 | Ascitic fluid cells | 3.8 | + |
| Dem-1 | Ascitic fluid cells | N.D. | + |
| Cas-1 | Ascitic fluid cells | 5.3 | + |
| Wad-1,2 | Ascitic fluid cells | 4.9 | N.D.* |

N.D. = not determined
*High background precluded detection

In the TRF assay, each tumor clump had significantly lower TRF lengths than associated normal cells. (See FIG. 10).

In the telomerase assay, significantly greater telomerase activity was evident in the ascitic fluid of certain patients than in the control tumor line HEY and purified tumor cell population, or the control cell line 293 CSH (FIG. 11; control cell line 293 CSH is shown in the two lanes located between the lane marked "ladder" and the lane marked "hey").

Example 8

Effect of HIV Infection on TRF Length

HIV infection leads to an acute viral infection manifesting itself as a virus-like syndrome, followed by a prolonged period of latency characterized by an absence of signs and symptoms. During this prolonged asymptomatic period (lasting usually 7–10 years), there is no diagnostic available for staging the course of the infection other than the presence or absence of antibodies to viral coat proteins. This does little to stage the disease or to help the physician measure the effectiveness of prophylactic agents.

While Meyaard et al., 257 *Science* 217, 1992, propose a programmed cell death for CD4$^+$ and CD8$^+$ cells of an HIV-infected individual, we propose that during those 7 to 10 years the immune system is able to keep the infection relatively repressed, but there is markedly increased turnover of the infected CD4$^+$ T-cells. This may be due in part to viral-mediated cell destruction. We propose that this essentially accelerates the replicative senescence of this particular subpopulation of T-cells, and with time results in a population of precursor pluripotent cells with markedly reduced proliferative capacity. Finally, this results in CD4$^+$ T-cells that are relatively unresponsive to stimuli to proliferate, as is typical of the replicative senescence of the cells observed in vitro.

We also propose that the replicative capacity of total peripheral lymphocytes or CD4$^+$ cells in particular, can be effectively determined by assaying telomere repeat length utilizing the method described above, e.q., with the oligonucleotide probe 5' TTAGGGTTAGGGTTAGGGTTAGGG (Seq. ID No. 8)(or one of similar or complementary sequence) hybridized to CD4$^+$ lymphocyte DNA isolated from the patient along with molecular size markers. These assays allow the physician to chart the course of the disease during the long intervening asymptomatic period, and to score the effectiveness of prophylactic therapeutics.

In order to determine whether TRF length is a useful marker in diagnosis of HIV infection, CD4$^+$ cell counting was performed on asymptomatic HIV-infected individuals, and compared to TRF length, measured as discussed above. As shown above, peripheral lymphocytes start with around 10 kb TRF length at birth, and reach a TRF length of 5.0 at approximately age 120. The results were as follows:

A 30 year old HIV+ with a CD4 count of 476 had a TRF of 7.6.

A 46 year old HIV− control, had a TRF of 7.0.

A 34 year old HIV+ with a CD4 count of 336, had a TRF of 7.7.

A 46 year old HIV− control, had a TRF of 7.1.

A 32 year old HIV+ with a CD4 count of 448, had a TRF of 6.9.

A 33 year old HIV+ with a CD4 count of 358, had a TRF of 5.0 (i.e., at a length observed for senescent cells)

The results indicate that the 33 year old HIV+ patient has a senescent telomere length in his CD4$^+$ cells, which means that they are at the end of their replicative capacity. In contrast, the CD4$^+$ count provided no indication of the status of this patient. Indeed, one patient actually had a lower CD4$^+$ count.

Two weeks after the assay was performed, this patient experienced a precipitous drop in CD4$^+$ count, going from 358 to 159, and was therefore diagnosed AIDS, and rapidly acquired leukoplakia on the tongue. The other patients remain asymptomatic. Thus, this diagnostic procedure is able to distinguish patients near the end of the course of HIV infection, whereas the previously used marker (CD4$^+$ count) could not.

The accelerated replicative senescence of CD4$^+$ lymphocytes during the course of HIV infection provides an appropriate indication for therapies designed to forestall telomere shortening, e.g., utilizing the CTO oligonucleotide described above. In addition, as described above, CD4+ cells of an individual at an early stage of infection can be banked for later administration to the individual. The efficacy of drugs, such as AZT, may also be determined to study whether the drug slows the rate of proliferation of CD4+ cells, and is thus useful at all stages of the disease. If not, it can be administered only when necessary during the course of the disease.

Example 9

Telomere Shortening in Human Mammary Epithelial (HME) Cells

Referring to FIG. 12, when digested with a restriction enzyme having 4-base recognition site (like Hinf1), most genomic DNA is digested into small fragments. However, because the repetitive telomeric sequences lack restriction sites, telomeres retain relatively large terminal restriction fragments (TRFs) composed of 2–4 Kb of subtelomeric DNA and age-dependent amounts of telomeric repeats. As previously described for human fibroblasts, lymphocytes and endothelial cells, telomere length shortens in normal human mammary epithelial cells during in vitro cellular senescence (compare TRF length in lanes 1 (PDL 21) and 2 (PDL 40)). In human mammary epithelial cells expressing E6 of human papilloma virus 16, the TRF length continues to shorten during the extended lifespan period until crisis and subsequently immortalization occurs (lane 3 (PDL 68)). The TRFs generally stabilize in immortalized cells (lane 4 (PDL 81) and lane 5 (PDL 107)) consistent with the re-expression of telomerase activity.

Example 10

Slowing Telomere Loss

Normal human mammary epithelial cells can be established from organoids (obtained from reduction mammoplasty) and can be cultured in defined condition in a standard medium (MCDB170) devoid of serum. Epithelial cells with typical cobblestone morphology spread around organoids plated in this medium. After the first subcultivation these cultures enter a period of growth arrest for 2–3 weeks until a population of small, highly birefringent and rapidly dividing cells expand among larger cells. The medium apparently selects for a less differentiated cell type with increased growth potential. These cells can be subcultured for 40–45 additional doublings before undergoing cellular senescence.

As in Example 1, a change in proliferative lifespan and rate of telomere shortening resulted in cultured mammary epithelial cells treated with the indicated amounts of CTO versus control random oligonucleotides. Normal human mammary epithelial cells from a donor (31) were infected with the E6 gene of human papilloma virus 16. This gene product degrades p53 protein and permits HME31 cells to have extended life span by proliferating from PDL 42 to PDL 62 when crisis occurs. During this extended lifespan period the TRFs shorten from an average of approximately 5 kb to 2.5 kb (compare in FIG. 12 HME31 PD 40 to HME31E6 PD 68).

As is demonstrated in FIG. 13, experiments initiated using HME31E6 cells at PDL 36 were cultured in the presence of 3, 10, 30 and 100 µM CTO. As controls the cells were cultured without oligonucleotides (nil) or with 30 µM random oligonucleotide. FIG. 13 demonstrates that compared to the nil control and the 30 µM random oligonucleotide, there was a dose related retardation of TRF shortening between PDL 36 and 50. This is most easily seen by examining the subpopulation of telomere TRFs that migrate more slowly than the rest, giving a discrete trailing band. Cells were maintained in logarithmic growth with medium changed and fresh oligonucleotide added three times per week.

Example 11

Extension of Life Span of IMR90 Fibroblasts

Referring to FIG. 14, IMR-90 lung fibroblasts at PDL 30 were treated with 10 µM, 30 µM or 100 µM phosphodiester CTO or with only media addition (control). The cells were cultured in medium containing regular defined supplemented calf serum. The cells were passaged in 24 well dishes and subcultivated by trypsinization upon reaching confluency at 25,000 cells per well. The cells were fed medium containing oligonucleotides at various concentrations daily. As a control, cells were fed identical medium without oligonucleotides. As is illustrated in FIG. 14, there was approximately a 12–15% extension of total life span with CTO. In these experiments the control cells divided approximately 15–18 times during the experiment, whereas the treated cells divided 23–26 times. IMR-90 telomeres shorten approximately 50 b.p. per division and the TRF length of the control IMR-90 fibroblasts at senescence was approximately 9 kb. Since the 100 µM CTO-treated IMR-90 cells senesced at PDL 55, the predicted difference in TRF length between the control and the 100 µM CTO (9 kb vs 9.4 kb) is too small to be resolved using current techniques.

Example 12

GTO Exoeriments

As in Example 2, an immortalized human fibroblast cell line, IDH4, which has very short TRFs, was incubated with GTO oligonucleotide. Referring to FIGS. 15 and 16, cells were incubated in regular culture medium containing serum in the presence of 10 µM, 30 µM and 100 µM GTO. The cells were fed fresh phosphodiester GTO oligonucleotide every other day and subcultured when confluent for a total of 90 days. The cells were still growing in GTO after 90 days at all concentrations used even though they grew more slowly at the higher GTO concentrations and went through fewer population doublings (control, 45 PDL; 10 µM GTO 40 PDL; 30 µM 35 PDL; 100 µM 25 PDL). When TRF analysis was performed after 90 days the IDH4 cells regained TRF length in a dose dependent manner with 30 µM and 100 µM being approximately the same (FIG. 15). This suggests that the presence of excess single-stranded TTAGGG DNA in the cell was probably influencing the feedback regulation of telomerase and actually increasing telomerase activity and extending telomere length. The control and 30 µM GTO were passaged without oligonucleotide addition for an additional 90 days (approximately 35–40 PDL). As is illustrated in FIG. 16, the TRFs slowly shorten.

These data and those in Example 2, indicate that cell lines differ in their response to GTO oligonucleotide. Thus, prior to use of such an oligonucleotide in therapeutic compositions it is important to ensure that the target cells respond as desired. Should the effect seen above occur, then the oligonucleotide should be chosen to change the response to that shown in Example 2. This can be done by choosing an oligonucleotide which binds to telomerase at a different site from that bound by GTO. Applicant believes that the effect observed above is caused by binding of GTO to required proteins, allowing telomerase to be active to expand the telomeres. Thus, by choosing an oligonucleotide which does not bind such proteins the desired effect of reducing telomerase activity can be achieved.

Compositions

Compositions or products according to the invention may conveniently be provided in the form of solutions suitable for parenteral or nasal or oral administration. In many cases, it will be convenient to provide an agent in a single solution for administration.

If the agents are amphoteric they may be utilized as free bases, as acid addition salts or as metal salts. The salts must, of course, be pharmaceutically acceptable, and these will include metal salts, particularly alkali and alkaline earth metal salts, e.g., potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrobromic acids. Such products are readily prepared by procedures well known to those skilled in the art.

The agents (and inhibitors) of the invention will normally be provided as parenteral compositions for injection or infusion. They can, for example, be suspended in an inert oil, suitably a vegetable oil such as sesame, peanut, or olive oil. Alternatively, they can be suspended in an aqueous isotonic buffer solution at a pH of about 5.6 to 7.4. Useful buffers include sodium citrate-citric acid and sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkali polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of agent which will be effective in one or multiple doses to perform a desired function. As will be recognized by those in the field, an effective amount of therapeutic agent will vary with many factors including the age and weight of the patient, the patient's physical condition, the blood sugar level to be obtained, and other factors.

Administration

Selected agents, e.g., oligonucleotide or ribozymes can be administered prophylactically, or to patients suffering from a target disease, e.g., by exogenous delivery of the agent to an infected tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of oligonucleotides are also suitable.

The specific delivery route of any selected agent will depend on the use of the agent. Generally, a specific delivery program for each agent will focus on naked agent uptake with regard to intracellular localization, followed by demonstration of efficacy. Alternatively, delivery to these same cells in an organ or tissue of an animal can be pursued. Uptake studies will include uptake assays to evaluate, e.g., cellular oligonucleotide uptake, regardless of the delivery vehicle or strategy. Such assays will also determine the intracellular localization of the agent following uptake, ultimately establishing the requirements for maintenance of steady-state concentrations within the cellular compartment containing the target sequence (nucleus and/or cytoplasm). Efficacy and cytotoxicity can then be tested. Toxicity will not only include cell viability but also cell function.

Some methods of delivery, e.g., for oligonucleotides, that may be used include:
a. encapsulation in liposomes,
b. transduction by retroviral vectors,
c. conjugation with cholesterol,
d. localization to nuclear compartment utilizing antigen binding site found on most snRNAs,
e. neutralization of charge of oligonucleotides by using nucleoti-de derivatives, and
f. use of blood stem cells to distribute oligonucleotides throughout the body.

At least three types of delivery strategies are useful in the present invention, including: agent modifications, particle carrier drug delivery vehicles, and retroviral expression vectors. Unmodified agents may be taken up by cells, albeit slowly. To enhance cellular uptake, the agent may be modified essentially at random, in ways which reduces its charge but maintains specific functional groups. This results in a molecule which is able to diffuse across the cell membrane, thus removing the permeability barrier.

Modification of agents to reduce charge is just one approach to enhance the cellular uptake of these larger molecules. The structural requirements necessary to maintain agent activity are well understood by those in the art. These requirements are taken into consideration when designing modifications to enhance cellular delivery. The modifications are also designed to reduce susceptibility to enzymatic degradation. Both of these characteristics should greatly improve the efficacy of the agent.

Chemical modifications of the phosphate backbone of oligonucleotides will reduce the negative charge allowing free diffusion across the membrane. This principle has been successfully demonstrated for antisense DNA technology. In the body, maintenance of an external concentration will be necessary to drive the diffusion of the modified oligonucleotides into the cells of the tissue. Administration routes which allow the diseased tissue to be exposed to a transient high concentration of the oligonucleotide, which is slowly dissipated by systemic adsorption are preferred. Intravenous administration with a drug carrier designed to increase the circulation half-life of the oligonucleotides can be used. The size and composition of the drug carrier restricts rapid clearance from the blood stream. The carrier, made to accumulate at the site of infection, can protect the oligonucleotides from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver agents to cells and that the agent remains biologically active.

For example, a liposome delivery vehicle originally designed as a research tool, Lipofectin, has been shown to deliver intact MRNA molecules to cells yielding production of the corresponding protein.

Liposomes offer several advantages: they are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nanoparticles and hydrogels may be potential delivery vehicles for an agent. These carriers have been developed for chemotherapeutic agents and protein-based pharmaceuticals.

Topical administration of agents is advantageous since it allows localized concentration at the site of administration with minimal systemic adsorption. This simplifies the delivery strategy of the agent to the disease site and reduces the extent of toxicological characterization. Furthermore, the amount of material to be applied is far less than that required for other administration routes. Effective delivery requires the agent to diffuse into the infected cells. Chemical modification of the agent to neutralize negative or positive charges may be all that is required for penetration. However, in the event that charge neutralization is insufficient, the modified agent can be co-formulated with permeability enhancers, such as Azone or oleic acid, in a liposome. The liposomes can either represent a slow release presentation vehicle in which the modified agent and permeability enhancer transfer from the liposome into the targeted cell, or the liposome phospholipids can participate directly with the modified agent and permeability enhancer in facilitating cellular delivery. In some cases, both the agent and permeability enhancer can be formulated into a suppository formulation for slow release.

Agents may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the agent to an accessible diseased or other tissue. Subcutaneous administration drains into a localized lymph node which proceeds through the lymphatic network into the circulation. The rate of entry into the circulation has been shown to be a function of molecular weight or size. The use of a liposome or other drug carrier localizes the agent at the lymph node. The agent can be modified to diffuse into the cell, or the liposome can directly participate in the delivery of either the unmodified or modified agent to the cell.

Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 10–2000 mg/kg of body weight/day. The duration of treatment will extend through the course of the disease symptoms, usually at least 14–16 days and possibly continuously. Multiple daily doses are anticipated for topical applications, ocular applications and vaginal applications. The number of doses will depend upon disease delivery vehicle and efficacy data from clinical trials.

Establishment of therapeutic levels of agent within the target cell is dependent upon the rate of uptake and degradation. Decreasing the degree of degradation will prolong the intracellular half-life of the agent. Thus, chemically modified agents, e.g., oligonucleotides with modification of the phosphate backbone, or capping of the 5' and 3' ends of the oligonucleotides with nucleotide analogues may require different dosaging.

It is evident from the above results, that by modulating telomerase activity and monitoring telomere length and telomerase activity, one may provide therapies for proliferative diseases and monitor the presence of neoplastic cells and/or proliferative capacity of cells, where one is interested in regeneration of particular cell types. Assays are provided which allow for the determination of both telomere length, particularly as an average of a cellular population, or telomerase activity of a cellular population. This information may then be used in diagnosing diseases, predicting outcomes, and providing for particular therapies.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method for diagnosis in a patient of a condition associated with an elevated level of human telomerase activity within one or more cells, the method comprising the steps of:
   determining the presence or amount of human telomerase within said cells; and
   correlating said presence or amount of telomerase with a condition associated with an elevated level of telomerase activity.

2. A method according to claim 1, wherein said presence or amount of telomerase is determined by detecting the presence of a component of telomerase.

3. A method according to claim 2, wherein said component is a protein component.

4. A method according to claim 3, wherein said detecting is by an antibody to said protein.

5. A method according to claim 4, wherein said antibody is a polyclonal antibody.

6. A method according to claim 4, wherein said antibody is a monoclonal antibody.

7. A method for diagnosis of cancer in a patient, the method comprising the steps of:
   determining the presence or amount of telomerase within said cells; and
   correlating said presence or amount of telomerase with cancer.

8. A method according to claim 7, wherein said presence or amount of telomerase is determined by detecting the presence of a component of telomerase.

9. A method according to claim 7, wherein said component is a protein component.

10. A method according to claim 9, wherein said detecting is by an antibody to said protein component.

11. A method according to claim 10, wherein said antibody is a polyclonal antibody.

12. A method according to claim 10, wherein said antibody is a monoclonal antibody.

13. A method according to claim 2 wherein the telomerase to be detected is a mammalian telomerase.

14. A method according to claim 13 wherein the mammalian telomerase is selected from the group consisting of equine, bovine, ovine, porcine, feline, and canine telomerase.

15. A method according to claim 13 wherein the mammalian telomerase is human telomerase.

16. A method according to claim 1 wherein the cells in or from which telomerase is to be detected are mammalian cells.

17. A method according to claim 16 wherein the mammalian cells are selected from the group of equine, bovine, ovine, porcine, feline, and canine cells.

18. A method according to claim 16 wherein the mammalian cells are human cells.

19. A method according to claim 1 wherein the condition associated with an elevated level of telomerase neoplasia.

20. A method according to claim 7 wherein the telomerase to be detected is a mammalian telomerase.

21. A method according to claim 20 wherein the mammalian telomerase is selected from the group consisting of equine, bovine, ovine, porcine, feline, and canine telomerase.

22. A method according to claim 20 wherein the mammalian telomerase is human telomerase.

23. A method according to claim 7 wherein the cells in or from which telomerase is to be detected are mammalian cells.

24. A method according to claim 23 wherein the mammalian cells are selected from the group consisting of equine, bovine, ovine, porcine, feline, and canine cells.

25. A method according to claim 23 wherein the mammalian cells are human cells.

26. A method according to claim 7 wherein the cancer to be diagnosed is selected from the group consisting of a carcinoma, sarcoma, leukemia, and lymphoma.

27. A method for diagnosis in a patient of a condition associated with an elevated level of mammalian telomerase activity within one or more cells, the method comprising the steps of:
   determining the presence or amount of mammalian telomerase within said cells; and
   correlating said presence or amount of telomerase with a condition associated with an elevated level of telomerase activity.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
( A ) LENGTH: 60
( B ) TYPE: nucleic acid
( C ) STRANDEDNESS: single
( D ) TOPOLOGY: linear ( i i ) SEQUENCE DESCRIPTION: SEQ ID NO: 1:

TTAGGGTTAG GGTTAGGGTT AGGGTTAGGG TTAGGGTTAG GGTTAGGGTT      50

AGGGTTAGGG      60

( 2 ) INFORMATION FOR SEQ ID NO: 2:

( i ) SEQUENCE CHARACTERISTICS:
( A ) LENGTH: 12
( B ) TYPE: nucleic acid
( C ) STRANDEDNESS: single
( D ) TOPOLOGY: linear ( i i ) SEQUENCE DESCRIPTION: SEQ ID NO: 2:

CCCTAACCCT AA      12

( 2 ) INFORMATION FOR SEQ ID NO: 3:

( i ) SEQUENCE CHARACTERISTICS:
( A ) LENGTH: 12
( B ) TYPE: nucleic acid
( C ) STRANDEDNESS: single
( D ) TOPOLOGY: linear ( i i ) SEQUENCE DESCRIPTION: SEQ ID NO: 3:

TTAGGGTTAG GG      12

( 2 ) INFORMATION FOR SEQ ID NO: 4:

( i ) SEQUENCE CHARACTERISTICS:
( A ) LENGTH: 18
( B ) TYPE: nucleic acid
( C ) STRANDEDNESS: single
( D ) TOPOLOGY: linear ( i i ) SEQUENCE DESCRIPTION: SEQ ID NO: 4:

CCCTAACCCT AACCCTAA      18

( 2 ) INFORMATION FOR SEQ ID NO: 5:

( i ) SEQUENCE CHARACTERISTICS:
( A ) LENGTH: 18
( B ) TYPE: nucleic acid
( C ) STRANDEDNESS: single
( D ) TOPOLOGY: linear ( i i ) SEQUENCE DESCRIPTION: SEQ ID NO: 5:

TTAGGGTTAG GGTTAGGG      18

( 2 ) INFORMATION FOR SEQ ID NO: 6:

( i ) SEQUENCE CHARACTERISTICS:
( A ) LENGTH: 24
( B ) TYPE: nucleic acid
( C ) STRANDEDNESS: single
( D ) TOPOLOGY: linear ( i i ) SEQUENCE DESCRIPTION: SEQ ID NO: 6:

CCCTAACCCT AACCCTAACC CTAA      24

( 2 ) INFORMATION FOR SEQ ID NO: 7:

```
( i ) SEQUENCE CHARACTERISTICS:
        ( A ) LENGTH: 13
        ( B ) TYPE: nucleic acid
        ( C ) STRANDEDNESS: single
        ( D ) TOPOLOGY: linear ( i i ) SEQUENCE DESCRIPTION: SEQ ID NO: 7:

CCCATTCCCA TTT                                                                    1 3

( 2 ) INFORMATION FOR SEQ ID NO: 8:

( i ) SEQUENCE CHARACTERISTICS:
            ( A ) LENGTH: 24
            ( B ) TYPE: nucleic acid
            ( C ) STRANDEDNESS: single
            ( D ) TOPOLOGY: linear ( i i ) SEQUENCE DESCRIPTION: SEQ ID NO: 8:

TTAGGGTTAG GGTTAGGGTT AGGG                                                        2 4
```